United States Patent
Comper

(10) Patent No.: US 6,589,748 B2
(45) Date of Patent: *Jul. 8, 2003

(54) METHOD FOR KIDNEY DISEASE DETECTION AND TREATMENT

(75) Inventor: Wayne D. Comper, Victoria (AU)

(73) Assignee: Monash University, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/892,797

(22) Filed: Jun. 28, 2001

(65) Prior Publication Data

US 2002/0022236 A1 Feb. 21, 2002

Related U.S. Application Data

(63) Continuation-in-part of application No. 09/415,217, filed on Oct. 12, 1999.

(30) Foreign Application Priority Data

Dec. 21, 1998 (AU) .......................................... PP7843/98

(51) Int. Cl.[7] ........................ G01N 33/53; G01N 33/00; C12Q 1/70

(52) U.S. Cl. ............................... 435/7.1; 435/3; 435/4; 435/5; 436/63; 436/86; 436/166; 436/811; 436/88

(58) Field of Search .................. 435/3, 4, 5, 7.1; 436/63, 86, 166, 811, 88

(56) References Cited

U.S. PATENT DOCUMENTS

| 5,246,835 A | 9/1993 | Suzuki et al. |
| 5,534,431 A | 7/1996 | McDonald |
| 5,654,158 A | 8/1997 | McDonald |
| 5,908,925 A | 6/1999 | Cohen et al. |

FOREIGN PATENT DOCUMENTS

| DE | 4336498 A1 | 4/1995 |
| EP | 514928 A2 | 11/1992 |
| JP | 6082446 | 3/1994 |
| WO | WO 00/37944 | 9/2000 |

OTHER PUBLICATIONS

*Proceedings of the Society for Experimental Biology and Medicine*, Dec. 1997. 216 (3):41423. Sabatino, B. and Van Liew, J.B., The renal handling of IgG in the aging rate and in experimental kidney disease.

*Kidney International*, Feb. 1991. 39(2):307–11. Ohta, K. et al., Urinary excretion of endothelin–1 in normal subjects and patients with renal disease.

*Journal of Chromatography*, Jul. 29, 1988. 429:3150–44. Weber, M.H., Urinary protein analysis.

*Clinical Nephrology*, Mar. 1979, 11(3): 140–41. Blainey, J.D. and Terry, J.M., Urinary fibrinogen degradation products and differential protein clearances in renal disease.

*British Medical Journal*, Feb. 22, 1975. 1(5955): 419–22. Hall, C.L. et al., Urinary fibrin–fibrinogen degradation products in nephrotic syndrome.

"Protein Degradation During Renal Passage in Normal Kidneys in Inhibited in Experimental Albuminuria", by Osicka et al., Clinical Science (1997) vol. 93, pp. 65–72.

"Fractional Clearance of Albumin is Influenced by its Degradation During Renal Passage", by Osicka et al., Clinical Science (1997) vol. 93, pp. 557–564.

(List continued on next page.)

*Primary Examiner*—Hankyel T. Park
*Assistant Examiner*—Stacy S. Brown
(74) *Attorney, Agent, or Firm*—McDermott, Will & Emery

(57) ABSTRACT

A method is disclosed for diagnosing early stage of a disease in which an intact protein found in urine is an indicator of the disease. The method includes assaying urine sample to detect the presence of modified protein using either immunological or non-immunological technique. Methods for preventing and treating the disease are also disclosed.

24 Claims, 15 Drawing Sheets

OTHER PUBLICATIONS

"Alterations in Renal Degradation of Albumin in Early Experimental Diabetes in the Rat: A New Factor in the Mechanism of Albuminuria"" by Burne et al., Clinical Science (1998), vol. 95, pp. 67–72.

"Glomerular Capillary Wall Permeability to Albumin and Horseradish Peroxidase", by Osicka et al., Nephrology 1996, vol. 2, pp. 199–212.

'The Return of Glomerular–Filtered Albumin to the Rat Renal Vein', by Eppel, et al., Kidney International, vol. 55, (1999), pp. 1861–1870.

"Glomerular Charge Selectivity for Anionic and Neutral Horseradish Peroxidase", by Osicka, et al., Kidney International, vol. 47 (1995), pp. 1630–1637.

Fractional Clearance of High Molecular Weight Proteins in Conscious Rats Using a Continuous Infusion Method, by Burne et al., Kidney International, vol. 55, (1999), pp. 261–270.

"Ramipril and aminoguanidine restore lysosomal processing in streptozotocin diabetic rats", T. M. Osicka et al., Diabetologia, (2001), pp. 230–236.

"Evaluation of a New Fluorescent Dye Method to Measure Urinary Albumin in Lieu of Urinary Total Protein", Alfredo A. Pegoraro, MD et al., American Journal of Kidney Diseases, vol. 35, No. 4 (Apr.), 2000, pp. 739–744.

Pharmacia Biotech BioDirectory catalog, p. 405. (1996).

BioRad Life Science Research Products catalog, p. 97. (1993).

Peak Results

| # | Name | Ret Time (min) | Area (uV*sec) | Height (uV) | Amount | Int Type |
|---|------|----------------|---------------|-------------|--------|----------|
| 1 |  | 4.117 | 329140 | 40683 |  | BB |
| 2 |  | 4.883 | 15767507 | 16240 |  | BB |
| 3 |  | 39.467 | 101020 | 6703 |  | BB |
| 4 |  | 40.000 | 46216 | 3171 |  | BB |
| 5 |  | 40.733 | 3138458 | 242228 |  | BV |
| 6 |  | 41.017 | 13063671 | 486192 |  | VB |
| 7 |  | 43.233 | 62005 | 5618 |  | BV |
| 8 |  | 43.700 | 33150 | 2909 |  | VB |
| 9 |  | 48.683 | 76368 | 3554 |  | BB |

Peak Results

| # | Name | Ret Time (min) | Area (uV*sec) | Height (uV) | Amount | Int Type |
|---|---|---|---|---|---|---|
| 1 | | 4.133 | 1802825 | 122050 | | BB |
| 2 | | 4.933 | 1874787 | 51415 | | BV |
| 3 | | 5.550 | 2903127 | 94067 | | VB |
| 4 | | 14.633 | 31135 | 3556 | | BB |
| 5 | | 15.617 | 54780 | 5951 | | BV |
| 6 | | 16.117 | 1518301 | 71355 | | VB |
| 7 | | 18.817 | 354458 | 32687 | | BB |
| 8 | | 28.717 | 16597 | 2098 | | BB |
| 9 | | 31.967 | 41230 | 4687 | | BB |
| 10 | | 32.567 | 107938 | 2454 | | BB |
| 11 | | 36.633 | 3763801 | 256381 | | BV |
| 12 | | 37.383 | 2135643 | 127492 | | VV |
| 13 | | 37.933 | 3054 | 972 | | VB |
| 14 | | 38.233 | 16226 | 2010 | | BB |
| 15 | | 38.950 | 8424624 | 387355 | | BV |

Peak Results

| # | Name | Ret Time (min) | Area (uV*sec) | Height (uV) | Amount | Int Type |
|---|------|----------------|---------------|-------------|--------|----------|
| 1 | | 4.067 | 2434486 | 185800 | | BV |
| 2 | | 4.483 | 16280311 | 1058547 | | VV |
| 3 | | 4.833 | 3864081 | 191585 | | VV |
| 4 | | 5.600 | 706286 | 46936 | | VV |
| 5 | | 5.983 | 6703449 | 371298 | | VV |
| 6 | | 7.133 | 451038 | 24299 | | VV |
| 7 | | 7.617 | 542790 | 22245 | | VB |
| 8 | | 9.600 | 3068571 | 128855 | | BV |
| 9 | | 10.333 | 151779 | 12552 | | VV |
| 10 | | 10.767 | 284984 | 25596 | | VV |
| 11 | | 11.017 | 919890 | 80160 | | VV |
| 12 | | 11.350 | 108494 | 10375 | | VV |
| 13 | | 11.650 | 738559 | 61334 | | VV |
| 14 | | 12.033 | 705972 | 48248 | | VV |
| 15 | | 12.200 | 429100 | 36385 | | VV |

Peak Results

| # | Name | Ret Time (min) | Area (uV*sec) | Height (uV) | Amount | Int Type |
|---|---|---|---|---|---|---|
| 1 | | 4.067 | 11142185 | 841146 | | BV |
| 2 | | 4.467 | 42897717 | 1567808 | | VV |
| 3 | | 5.333 | 2771843 | 185077 | | VV |
| 4 | | 5.750 | 16970479 | 962668 | | VV |
| 5 | | 6.433 | 1506454 | 80128 | | VV |
| 6 | | 6.800 | 1187124 | 68430 | | VV |
| 7 | | 7.150 | 1105355 | 55641 | | VV |
| 8 | | 7.500 | 322563 | 40826 | | VV |
| 9 | | 7.633 | 1108215 | 42173 | | VV |
| 10 | | 8.183 | 522250 | 36801 | | VV |
| 11 | | 8.400 | 1110198 | 40131 | | VV |
| 12 | | 9.317 | 7318394 | 222305 | | VV |
| 13 | | 10.400 | 866046 | 57467 | | VV |
| 14 | | 10.667 | 2300590 | 148511 | | VV |
| 15 | | 11.050 | 399236 | 32665 | | VV |

Peak Results

| # | Name | Ret Time (min) | Area (uV*sec) | Height (uV) | Amount | Int Type |
|---|---|---|---|---|---|---|
| 1 | | 4.083 | 10518737 | 792810 | | BV |
| 2 | | 4.367 | 14687929 | 1410889 | | VV |
| 3 | | 4.533 | 22637504 | 1494339 | | VV |
| 4 | | 5.163 | 3593396 | 219436 | | VV |
| 5 | | 5.717 | 22692299 | 1152174 | | VV |
| 6 | | 6.817 | 960777 | 60477 | | VV |
| 7 | | 7.150 | 682488 | 44596 | | VV |
| 8 | | 7.500 | 1795219 | 58004 | | VV |
| 9 | | 8.250 | 1518279 | 43057 | | VV |
| 10 | | 9.250 | 7251773 | 190341 | | VV |
| 11 | | 10.367 | 1000343 | 60821 | | VV |
| 12 | | 10.633 | 1192302 | 77226 | | VV |
| 13 | | 11.050 | 2788523 | 178468 | | VV |
| 14 | | 11.417 | 6160036 | 248690 | | VV |
| 15 | | 12.200 | 4008326 | 298350 | | VV |

Peak Results

| # | Name | Ret Time (min) | Area (uV*sec) | Height (uV) | Amount | Int Type |
|---|------|----------------|---------------|-------------|--------|----------|
| 1 | | 4.100 | 2979946 | 236299 | | BV |
| 2 | | 4.450 | 15028113 | 921410 | | VV |
| 3 | | 4.817 | 4812815 | 249684 | | VV |
| 4 | | 5.550 | 814070 | 71678 | | VV |
| 5 | | 5.850 | 9688029 | 563550 | | VV |
| 6 | | 6.600 | 914291 | 48992 | | VV |
| 7 | | 7.000 | 272597 | 28204 | | VV |
| 8 | | 7.250 | 1918070 | 53043 | | VV |
| 9 | | 8.267 | 1161101 | 29288 | | VV |
| 10 | | 9.367 | 9258559 | 294071 | | VV |
| 11 | | 10.617 | 903487 | 62562 | | VV |
| 12 | | 10.833 | 1216206 | 83275 | | VV |
| 13 | | 11.250 | 178790 | 15563 | | VV |
| 14 | | 11.550 | 532841 | 42407 | | VV |
| 15 | | 11.867 | 1315340 | 70286 | | VV |

METHOD FOR KIDNEY DISEASE DETECTION AND TREATMENT

CROSS-REFERENCE TO RELATED APPLICATION

This application is a Continuation-in-Part of and claims priority to parent application Ser. No. 09/415,217, filed Oct. 12, 1999.

FIELD OF THE INVENTION

The present invention relates to methods of detecting an early stage of renal disease and/or renal complications of a disease. The invention also relates to preventing and treating the disease.

BACKGROUND OF THE INVENTION

The appearance of excess protein such as albumin in the urine is indicative of kidney disease. Diabetic nephropathy is such a disease. By the time the excess albumin is detected, kidney disease has progressed, possibly to a stage where it is irreversible and treatment has little effect. Therefore it is an object of the invention to provide a test that is more sensitive than the currently known radioimmunoassay to detect such a disease as early as possible so that the disease can be either prevented or a treatment protocol commenced early on in the disease.

Specific proteinuria, and in particular, albuminuria (micro- and macro-), is a marker of disease including renal disease (glomerulonephritis, bacterial and viral glomerulonephritides, IgA nephropathy and Henoch-Schönlein Purpura, membranoproliferative glomerulonephritis, membranous nephropathy, Sjögren's syndrome, diabetic nephropathy, nephrotic syndrome (minimal change disease, focal glomerulosclerosis and related disorders), acute renal failure, acute tubulointerstitial nephritis, pyelonephritis, GU tract inflammatory disease, Preclampsia, renal graft rejection, leprosy, reflux nephropathy, nephrolithiasis), genetic renal disease (medullary cystic, medullar sponge, polycystic kidney disease (autosomal dominant polycystic kidney disease, autosomal recessive polycystic kidney disease, tuborous sclerosis), von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies), monoclonal gammopathies (multiple myeloma, amyloidosis and related disrders), febrile illness (familial Mediterannean fever, HIV infection—AIDS), inflammatory disease (systemic vasculitides (polyarteritis nodosa, Wegener's granulomatosis, polyarteritis, necrotizing and crescentic glomerulonephritis), polymyositisdermatomyositis, pancreatitis, rheumatoid arthritis, systemic lupus erythematosus, gout), blood disorders (sickle cell disease, thrombotic thrombocytopenia purpura, hemolytic-uremic syndrome, acute corticol necrosis, renal thromboembolism), trauma and surgery (extensive injury, bums, abdominal and vascular surgery, induction of anesthesia), drugs (penicillamine, steroids) and drug abuse, malignant disease (epithelial (lung, breast), adenocarcinoma (renal), melanoma, lymphoreticular, multiple myeloma), circulatory disease (myocardial infarction, cardiac failure, peripheral vascular disease, hypertension, coronary heart disease, non-atherosclerotic cardiovascular disease, atherosclerotic cardiovascular disease), skin disease (psoriasis, systemic sclerosis), respiratory disease (COPD, obstructive sleep apnoea, hypoia at high altitude) and endocrine disease (acromegaly, diabetes mellitus, and diabetes insipidus).

Kidney disease may result from bacterial infection, allergies, congenital defects, stones, antibiotics, immunosuppressives, antineoplastics, nonsteroidal anti-inflammatory drugs, analgesics, heavy metals, tumors, chemicals.

The applicant has found that proteins, including albumin, are normally excreted as a mixture of native protein and fragments that are specifically produced during renal passage (Osicka, T. M. et al. (1996) *Nephrology*, 2, 199–212). Proteins are heavily degraded during renal passage by post-glomerular (basement membrane) cells, which may include tubular cells. Lysosomes in renal tubular cells may be responsible for the breakdown of proteins excreted during renal passage (see FIG. 1). The breakdown products are excreted into the tubular lumen. In normal individuals, most of the albumin in the urine is fragmented.

When lysosome activity or intracellular processes directing substrates to lysosomes is reduced, more of the high molecular weight, and substantially full length albumin appears in the urine. This reflects an imbalance in the cellular processes in the kidney tissue.

Until now, it was thought that conventional radioimmunoassay was suitable for detecting all (total) of a specific protein in a sample. But the total content of the protein may include more than those that are identifiable by known antibodies using conventional radioimmunoassay (RIA). Currently available radioimmunoassays rely on antibodies to detect proteins such as albumin. Antibody detection is very accurate down to nanogram levels. However, the specificity of the antibodies influences detection of the protein. The antibody detects certain epitopes. If the specific epitope on the albumin is absent, altered or masked, or the albumin is modified in any other way so that the antibody fails to detect the albumin, conventional radioimmunoassays may not provide a true representation of the true amount of albumin present in a urine sample.

Methods of detecting early signs of a disease, including kidney disease, determining a patient's propensity for the disease, preventing the onset of the disease, and treating the disease at the earliest stage possible, as well as a method for determining the total content of a specific protein in a sample, are some of the objects of the invention.

SUMMARY OF THE INVENTION

The present invention is directed to a method of diagnosing early stage of renal disease and/or renal complications of a disease, comprising:

(a) separating all of the proteins in a urine sample; and
(b) detecting a modified form of a protein in the sample, wherein detection of the modified protein is indicative of an early stage of the renal disease and/or renal complications of a disease.

Although not limited to any particular disease, according to the method of the invention, the disease sought to be diagnosed includes nephropathy, diabetes insipidus, diabetes type I, diabetes II, renal disease (glomerulonephritis, bacterial and viral glomerulonephritides, IgA nephropathy and Henoch-Schönlein Purpura, membranoproliferative glomerulonephritis, membranous nephropathy, Sjögren's syndrome, nephrotic syndrome (minimal change disease, focal glomerulosclerosis and related disorders), acute renal failure, acute tubulointerstitial nephritis, pyelonephritis, GU tract inflammatory disease, Pre-clampsia, renal graft rejection, leprosy, reflux nephropathy, nephrolithiasis), genetic renal disease (medullary cystic, medullar sponge, polycystic kidney disease (autosomal dominant polycystic kidney disease, autosomal recessive polycystic kidney disease, tuborous sclerosis), von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies), monoclonal gammopathies (multiple myeloma, amyloidosis and related disorders), febrile illness (familial Mediterranean fever, HIV infection—AIDS), inflammatory disease (systemic vasculitides (polyarteritis nodosa, Wegener's granulomatosis, polyarteritis, necrotizing and crescentic glomerulonephritis), polymyositis-dermatomyositis, pancreatitis, rheumatoid arthritis, systemic lupus erythematosus, gout), blood disorders (sickle cell disease, thrombotic thrombocytopenia purpura, hemolytic-uremic syndrome, acute cortical necrosis, renal thromboembolism), trauma and surgery (extensive injury, burns, abdominal and vascular surgery, induction of anesthesia), drugs (penicillamine, steroids) and drug abuse, malignant disease (epithelial (lung, breast), adenocarcinoma (renal), melanoma, lymphoreticular, multiple myeloma), circulatory disease (myocardial infarction, cardiac failure, peripheral vascular disease, hypertension, coronary heart disease, non-atherosclerotic cardiovascular disease, atherosclerotic cardiovascular disease), skin disease (psoriasis, systemic sclerosis), respiratory disease (COPD, obstructive sleep apnoea, hypoia at high altitude) and endocrine disease (acromegaly, diabetes mellitus, diabetes insipidus).

In addition, the method can be practiced using any protein, preferably, albumin, globulin ($\alpha$-globulin($\alpha_1$-globulin, $\alpha_2$-globulin),$\beta$-globulin,$\gamma$-globulin), euglobulin, pseudoglobulin I and II, fibrinogen, $\alpha_1$ acid glycoprotein (orosomucoid), $\alpha_1$ glycoprotein, $\alpha_1$ lipoprotein, ceruloplasmin, $\alpha_2$ 19 S glycoprotein, $\beta_1$ transferrin, $\beta_1$ lipoprotein, immunoglobulins A, E, G, and M, horseradish peroxidase, lactate dehydrogenase, glucose oxidase, myoglobin, lysozyme, protein hormone, growth hormone, insulin, or parathyroid hormone.

The method can be practiced using non-antibody means, using such methods as chromatography, electrophoresis, or sedimentation, which further include such methods as partition chromatography, adsorption chromatography, paper chromatography, thin-layer chromatography, gas-liquid chromatography, gel chromatography, ion-exchange chromatography, affinity chromatography, or hydrophobic interaction chromatography, moving-boundary electrophoresis, zone electrophoresis, or isoelectric focusing. Albumin detection with specific albumin dyes may also be used.

In particular, the method of the invention is directed to using a hydrophobic interaction chromatography in a high-pressure liquid chromatography (HPLC) apparatus.

The present invention is also directed to an antibody detecting method for diagnosing early stage of renal disease and/or renal complications of a disease. The method of the invention is accomplished by assaying for an intact/modified protein that is not normally identifiable in urine using conventional means. The intact/modified protein of the invention is present in the urine sample of a diseased person or a person who is predisposed to a disease before the native protein can be detected. Therefore, the detection of an intact/modified protein in a urine sample indicates at an early stage that the subject is either diseased or predisposed to the disease, even though the subject may otherwise appear to be normal. An assay method of the invention includes detecting an intact/modified protein by an antibody specific for both the modified and unmodified forms of the protein.

Preferably, the antibody is specific for the modified protein. The antibody can be attached to an enzymatic, radioactive, fluorescent or chemiluminescent label, wherein the detecting step comprises radioimmunoassay, immunoradiometric assay, fluorescent immunoassay, enzyme linked immunoassay, or protein A immunoassay.

In the method of the invention, the early stage of the disease is diagnosed when the modified protein is present in the urine in increasing amounts over time, and conventional radioimmunoassay does not detect the modified protein.

The present invention is also directed to an article of manufacture for diagnosing an early stage of renal disease and/or renal complications of a disease, comprising:

(a) a container comprising a labeled antibody specific for a modified form of the protein;

(b) a container comprising reagents for developing antibody reaction; and (c) instructions on how to use components (a) and (b) to carry out the diagnosis.

In addition, the present invention is also directed to a method for determining a treatment agent for renal disease and/or renal complications of a disease, comprising:

(a) administering to a person in need thereof an agent that is suspected of being able to treat the disease;

(b) obtaining a urine sample from the person; and (c) assaying for a modified form of the protein in the sample, wherein either presence or lack of presence of the modified form of the protein in the urine or decreasing amount of the modified form of the protein over time indicates that the agent is a treatment agent for the renal disease and/or renal complications of a disease.

The invention is also directed to a method for treating a person suffering from a disease in which a diseased state is indicated by specific proteinuria, comprising administering a therapeutically effective amount of the treatment agent obtained according to the above method to a person in need thereof. Preferably, the treatment agent is a lysosome activating compound.

Another object of the invention is to determine the sum of modified and unmodified forms of a of a specific protein in a sample, comprising:

(a) separating all of the proteins in the sample;

(b) detecting modified and unmodified forms of the specific protein; and (c) integrating the modified and unmodified forms of the specific protein to determine the sum of the specific protein in the sample.

Preferably, the sample is a biological sample, such as urine.

These and other objects of the invention will be more fully understood from the following description of the invention, the referenced drawings attached hereto and the claims appended hereto.

DETAILED DESCRIPTION OF THE INVENTION

The applicant has discovered that when proteins, including major plasma proteins such as albumin and immunoglobulin, are filtered by the kidney they are subsequently degraded by cells in the kidney prior to the material being excreted. It is likely that filtered proteins are taken up by tubular cells. Tubular cells lie beyond the kidney filter and come in direct contact with the primary filtrate. When proteins are internalized by the tubular cells, they are directed towards the lysosomes, where they are partially degraded to various size fragments, and then regurgitated to outside the cell. These regurgitated fragments, of which there may be at least 60 different fragments generated from any one particular type of protein, are then excreted into the urine.

The applicant has discovered that in renal disease fragmentation of proteins is inhibited. This means that substantially full-length filtered proteins will be excreted in a person suffering from renal disease. This transition from fragmentation to inhibition of fragmentation of excreted proteins is a basis for the development of new drugs and diagnostic assays. For example, initial changes that occur with the onset of renal complications in diabetes are associated with a change in the fragmentation profile of excreted albumin. This leads to an apparent microalbuminuria, which is synonymous with the development of diabetic nephropathy. It is likely that this is due to an inhibition in the lysosomal activity of tubular cells in diabetes. Thus, drugs can be formulated to turn on lysosomal activity in diabetes where renal complications are occurring. The drugs may also be useful in other renal diseases where lysosomal activities are affected, or in diabetes without renal complications in situations where lysosomal activity is turned off in non renal tissues. Such drugs include antiproliferative drugs, such as anti cancer drugs or antibodies to neutralize TGF beta.

The applicant has discovered a unique assay for detecting modified forms of specific proteins, which are detected in the urine of certain subjects before the unmodified form of the specific protein is detected using conventional assays, such as radioimmunoassays. Detection of the modified protein is predictive of a predisposition to renal disease.

Definitions

"Fragmented protein or fragment albumin" includes postglomerular breakdown products after chemical, enzymatic or physical breakdown that occurs during renal passage. These components have a reduced size and/or may have changed hydrophobicity.

Figure 5:
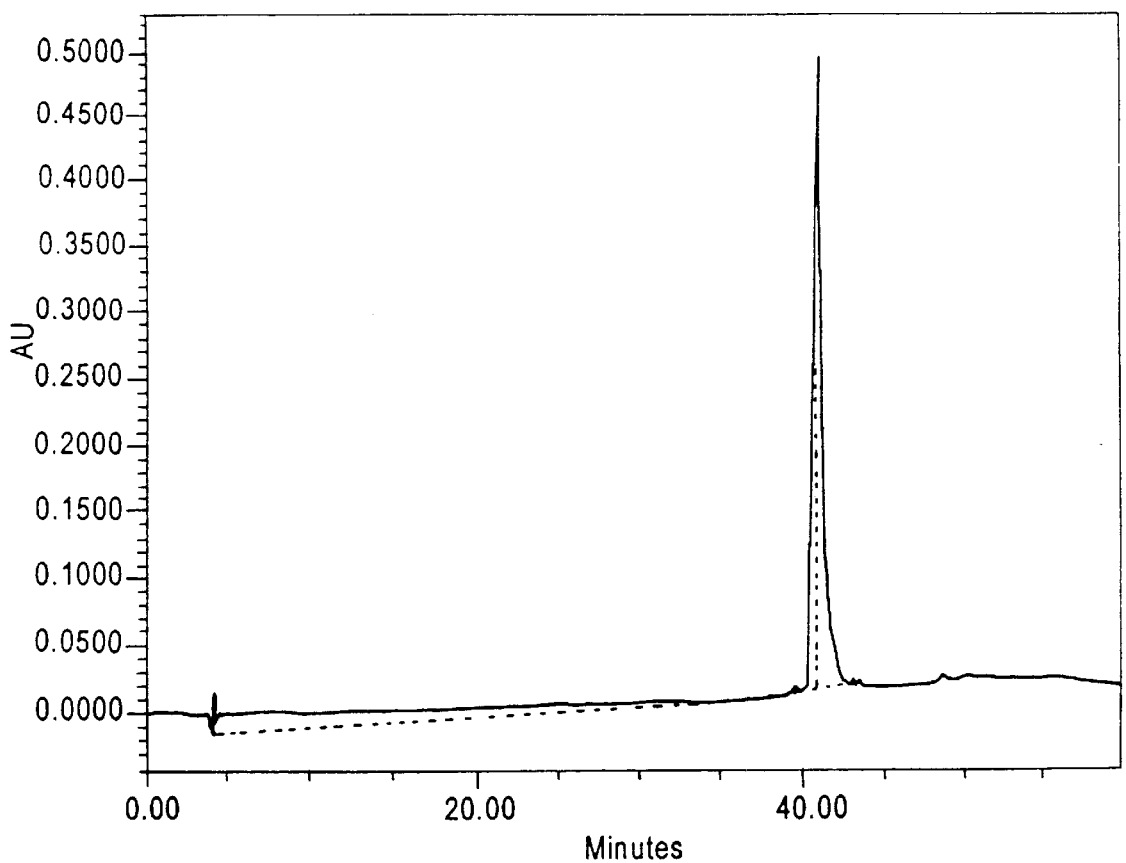
FIG. 5 illustrates a HPLC profile of albumin alone.

"Intact albumin, modified albumin, or modified form of albumin" as used herein means a compound having similar size and structural characteristics to native albumin, wherein the amino acid sequence is substantially the same as the native albumin. It is preferably a filtered intact protein. It elutes at or near the same position as native albumin on high-pressure liquid chromatography (HPLC) (FIG. 5). However, the structure has been modified biochemically either by minor enzyme mediated modification or addition to its basic structure and/or physically through a change in its three dimensional structure so that it escapes detection by conventionally used anti-albumin antibodies. Biochemical modification may be made by enzymes such as endo- or exo-peptidases. The 3D structure of albumin may have been altered in some way. Ligands may have bound to the albumin, or it may be any combination of these. The modified albumin detected in the method of the invention is not detectable by current and conventional radioimmunoassays using available antibodies and is not a fragment.

Conventional anti-albumin antibodies can be purchased from any purveyor of immunochemicals. For example, monoclonal antibody catalog numbers A6684 (clone no. HSA-11), and A2672 (clone no. HSA-9), as well as liquid whole serum, lyophilized fractionates, liquid IgG fraction, and the monoclonal antibodies in liquid ascites fluids form, can be obtained from Sigma, St. Louis, Mo., as found in the Immunochemicals section at pages 1151–1152 in the 1994 Sigma—Biochemicals Organic Compounds for Research and Diagnostic Reagents catalog.

As used herein, intact/modified albumin includes albumin that is substantially full-length, fragmented, chemically modified, or physically modified. As used herein, intact/modified albumin is meant to indicate albumin that is less than, equal to, or greater in molecular weight than the full-length albumin, and elutes at or near the native albumin position in a separation medium, such as chromatography, preferably HPLC, and most preferably hydrophobicity HPLC. As used herein, fragmented albumin is meant to refer to the fragment of albumin that is not detected by conventional anti-albumin antibody, and its presence is detected in diagnosing an early stage of renal disease and/or renal complications of a disease. The detection of the presence of intact/modified albumin is an indication of a predisposition to renal disease.

"Intact protein, modified protein or modified form of a protein" as used herein includes those forms of substantially full-length protein which are undetectable by conventional radioimmunoassay. The protein includes, but is not limited to, albumins, globulins ($\alpha$-globulin($\alpha_1$-globulin, $\alpha_2$-globulin),$\beta$-globulins,$\gamma$-globulins), euglobulins, pseudoglobulin I and II, fibrinogen, $\alpha_1$ acid glycoprotein (orosomucoid), $\alpha_1$ glycoprotein, $\alpha_1$ lipoproteins, ceruloplasmin, $\alpha_2$ 19 S glycoprotein, $\beta_1$ transferrin, $\beta_1$ lipoprotein, immunoglobulins A, E, G, and M, protein hormones including growth hormone, insulin, parathyroid hormone and other proteins including horseradish peroxidase, lactate dehydrogenase, glucose oxidase, myoglobin, and lysozyme.

"Kidney disease" as used herein includes any malfunction of the kidney. Kidney disease may be identified by the presence of intact or modified albumin in the urine. Preferably, an early diagnosis of the kidney disease may be made by detecting the presence of modified protein in the urine, or an increase in the modified protein in the urine over time.

"Low lysosome activity" as used herein is compared against normal levels of lysosome activity and/or lysosome machinery that traffics protein to the lysosome in a normal individual. The activity is insufficient for the lysosome to fragment proteins so that intact protein is excreted at a greater amount than at normally low levels.

"Lysosome-activating compound" as used herein refers to a compound that is beneficial to reactivation of the lysosome. The compound may work directly or indirectly on the lysosome resulting in activation of lysosomal function. These compounds may be selected from the group including, but not limited to, anticancer compounds, anti-proliferation compounds, paracetamol, vitamin A (retinoic acid) or derivatives of retinol, or compounds, including antibodies, to neutralize TGF beta.

"Macroalbuminuria" is a condition where an individual excretes greater than 200 $\mu$g albumin/min in the urine as measured by conventional radioimmunoassay (RIA).

"Microalbuminuria" is a condition where an individual excretes at least 20 $\mu$g albumin/min in the urine as measured by conventional radioimmunoassay (RIA). RIA measures down to 15.6 ng/ml and is able to measure albumin in urine of normal subjects who have clearance of less than 6 $\mu$g/min. However, when albumin excretion exceeds 20 $\mu$g/min, treatment of the kidney disease is limited and full recovery is difficult from this point.

"Microalbuminuric" as used herein is a condition when albumin is detected in the urine at an excretion rate of at least 20 $\mu$g/min as measured by conventional RIA.

As used herein, "native" and "unmodified" are used interchangeably to describe a protein that is naturally found in an organism, preferably a human, which has not been modified by the filtering process of the renal glomeruli.

"Normal individual" as used herein is an individual who does not have a disease in which intact protein found in urine is an indicator of the disease. Preferably, the disease is kidney disease.

"Normal levels of lysosome activity" are levels of lysosome activity found in undiseased kidney of a normal individual.

"Normoalbuminuric" as used herein means a condition where albumin is excreted in the urine and is not detectable by RIA, or less than 20 $\mu$g/min (as measured by RIA) is excreted.

"Propensity for a disease" as used herein means that a disease may result in an individual as judged by a determination of the presence and excretion rate of a modified protein such as modified albumin.

"Proteinuria" as used herein is the existence of protein in the urine, usually in the form of albumin, a protein that is soluble in water and can be coagulated by heat. Related to this, "specific proteinuria" refers to the existence of a particular protein in the urine.

"Radioimmunoassay" as used herein is a method for detection and measurement of substances using radioactively labeled specific antibodies or antigens.

"Reactivation of the lysosome" as used herein includes an activation of lysosome activity preferably so that breakdown of proteins, particularly albumin, is increased compared with an inactivated state of the lysosome.

"Restore" as used herein means to restore in full or in part so that the component being restored has an improved function compared with its previous function.

The "sum of intact and intact modified protein" as used herein refers to the total amount of intact protein, and intact modified protein present in a biological sample.

"Total protein" as used herein refers to a particular filtered protein present in native, unmodified, modified or fragmented form that is excreted in urine. It includes protein that is not detected by conventional radioimmunoassay or conventional methods, which are currently available to detect the protein. Preferably the protein is albumin.

According to the present invention, the diseases to be treated include, but are not limited to renal disease (glomerulonephritis, bacterial and viral glomerulonephritides, IgA nephropathy and Henoch-Schönlein Purpura, membranoproliferative glomerulonephritis, membranous nephropathy, Sjögren's syndrome, diabetic nephropathy, nephrotic syndrome (minimal change disease, focal glomerulosclerosis, and related disorders), acute renal failure, acute tubulointerstitial nephritis, pyelonephritis, GU tract inflammatory disease, Pre-clampsia, renal graft rejection, leprosy, reflux nephropathy, nephrolithiasis), genetic renal disease (medullary cystic, medullar sponge, polycystic kidney disease (autosomal dominant polycystic kidney disease, autosomal recessive polycystic kidney disease, tuborous sclerosis), von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies)

In one aspect of the invention, there is provided a method for determining a propensity for or early diagnosis of renal disease and/or renal complications of a disease. The method includes determining a change in the albumin content in a urine sample. The disease may be a kidney disease, although not necessarily limited to a kidney disease.

In the method of the invention, albumin is used herein only as an example of a protein to be detected in urine. When the albumin in a patient is analyzed by conventional RIA, it is expected that a normoalbuminuric patient or normal individual would have albumin in the urine in the range of 3–10 $\mu$g/min in young people and greater in older people. However, normoalbuminuric patients also show levels of albumin in the urine if measured by HPLC. Applicant has found that these levels may be in the order of 5 $\mu$g/min. As kidney disease progresses, the level of intact/modified albumin will increase to microalbuminuria levels in the order of 20 to 200 $\mu$g/min as determined by RIA. This will be much higher when determined by HPLC or a method that determines the sum of intact albumin and intact modified albumin. By monitoring the increase in intact/modified albumin, early signs of kidney disease may be detected. However, these levels are not detectable by the methods currently available such as radioimmunoassay using antibodies currently commercially in use, possibly for the reason that antibodies detect certain epitopes. If the albumin is modified in any way as described above, the epitope may be destroyed thereby leaving the modified albumin undetectable.

A patient suspected of having diabetic kidney disease will not show signs of kidney degeneration until well after 10 to 15 years when albumin is detected by currently available methods such as RIA methods. Urinary excretion rates of at least 20 $\mu$g/min may be detected by RIA when an individual enters a microalbuminuric state. Again, by observing the excretion of modified albumin, a change in the kidney and possibly onset of a kidney disease may be detected.

A normoalbuminuric subject, or normoalbuminuric diabetic patient may continue to have a low albumin excretion rate of less than 20 $\mu$g/min as determined by RIA, for many years. The presence of albumin in the urine is a sign that functions of the kidney may be impaired. Once this level begins to change, treatment may be initiated.

In a normal individual a small amount of albumin is detectable in the urine. Total filtered albumin appears mainly as fragmented albumin in urine. Some albumin may be detected in normoalbuminuric individuals. However, the excretion rate of albumin in urine in a normoalbuminuric individual may be as low as 5 $\mu$g/min. This level is generally detectable by RIA.

The modified protein of the invention can be detected by a variety of methods that are well-known in the art, including, but not limited to chromatography, electrophoresis and sedimentation, or a combination of these, which are described in Karger B L, Hancock W S (eds.) *High Resolution Separation and Analysis of biological Macromolecules. Part A Fundamentals in Methods in Enzymology*, Vol. 270, 1996, Academic Press, San Diego, Calif., USA; Karger B L, Hancock W S (eds.) *High Resolution Separation and Analysis of biological Macromolecules. Part B Applications in Methods in Enzymology*, Vol. 271, 1996, Academic Press, San Diego, Calif., USA; or Harding S E, Rowe, A J, Horton J C (eds.) *Analytical Ultracentrifugation in Biochemistry and Polymer Science.* 1992, Royal Soc. Chemistry, Cambridge, UK, which references are incorporated herein by reference in their entirety.

The electrophoresis method includes, but is not limited to, moving-boundary electrophoresis, zone electrophoresis, and isoelectric focusing.

The chromatography method includes, but is not limited to, partition chromatography, adsorption chromatography, paper chromatography, thin-layer chromatography, gas-liquid chromatography, gel chromatography, ion-exchange chromatography, affinity chromatography, and hydrophobic interaction chromatography. Preferably, the method is a sizing gel chromatography and hydrophobic interaction chromatography. More preferably, the method is hydrophobic interaction chromatography using a HPLC column.

The modified protein can also be detected by the use of specific albumin dyes. Such methods are described for example by Pegoraro, et al. *American Journal of Kidney Diseases,* Vo. 35, No. 4, April, 2000, pp. 739–744, the entire disclosure of which is hereby incorporated by reference. The modified albumin, as well as whole albumin, are detectable by this dye method to provide the sum of modified albumin and whole or intact albumin. This detection method may be used with or without an initial separation of the albumin components form urine. Such dyes normally do not detect fragments <10,000 in molecular weight, but will detect the modified albumin.

In this dye method of detection, a dye such as Albumin Blue 580, is used. Such dyes are naturally non-fluorescent but fluoresce on binding to intact albumin as well as the modified albumin, but do not bind to globulins. Therefore, globulins do not interfere with the assay so that measurements can be made in unfractionated urine.

Applicant has found that among diabetics, a normoalbuminuric diabetic patient has almost undetectable levels of modified or fragments of albumin when analyzed by conventional RIA. They appear to be normal. However, when the urine is tested by HPLC, the levels of modified albumin are much greater than found in a normal individual. This difference in albumin may be attributed to the inability of conventional RIA's to adequately detect all albumin (total albumin) in intact or modified forms. Thus, HPLC is preferred for generating a fragmentation profile. A fragmentation profile on HPLC is characterized by a series of peaks representing a number of species of albumin as fragments or in intact or modified forms.

In a preferred aspect of the present invention, the method of determining a propensity for or early diagnosis of a kidney disease in a subject is determined before the subject becomes microalbuminuric.

Measuring albumin content in a sample by an HPLC method of the present invention may provide different results from its measurement by conventional RIA. In the HPLC technique, a low level of albumin is observed in normal individuals. When the level of modified albumin begins to be detected and its level increases, and progresses toward microalbuminuria then a patient can be determined to have a propensity for kidney disease.

In a normal individual, the HPLC generated fragmentation profile is characterized by the absence of a peak in a region where full-length native albumin elutes. Instead, multiple fragmented albumin is detectable. A pure protein product (unmodified) produces essentially a single peak. For example, using a hydrophobicity HPLC, albumin was observed to elute in the range of 39–44 minutes (FIG. 5). Thus, a normal individual would provide a distinct fragmentation profile indicative of an absence of kidney disease or no propensity for a kidney disease. However, as kidney disease progresses, an increasing amount of modified albumin first, and then native form later are detectable. The fragmentation profile begins to change and more products in the region of full-length albumin manifests as additional spikes or an enlarged peak indicative of more intact/modified albumin in the urine.

In a HPLC generated fragmentation profile of a urine sample, the modified albumin may appear in a region where native albumin elutes but may be manifest as multiple peaks indicating the presence of multiple forms of modified albumin.

In a further preferred embodiment, the propensity for kidney disease may be measured by determining the presence of or identifying at least one species of modified albumin. This may be determined or identified by the presence of a specific peak on a HPLC profile, preferably the peak is within the range of position that corresponds to the elution position of the native albumin.

A HPLC column for detecting modified albumin or unmodified albumin may be a hydrophobicity column, such as Zorbax 300 SB-CB (4.6 mm×150 mm). A 50 $\mu$l sample loop may be used. Elution solvents suitable for HPLC in detecting albumin and its breakdown products may include standard elution solvents such as acetonitrile solvents. Preferably a buffer of water/1% trifluoro acetic acid (TFA) followed by a buffer of 60% acetonitrile/0.09% TFA may be used. A gradient of 0 to 100% of a 60% acetonitrile/0.09% TFA has been found to be suitable.

Suitable HPLC conditions for a hydrophobicity column may be as follows:

Solvent A H$_2$O, 1% trifluoro acetic acid
Solvent B 60% acetonitrile, 0.09% TFA
Solvent A2 99.96>00.00:49.58 min
Pressure 9.014Mpascalls (~1100 psi)
Solvent B2 0.04>100.0:49.58 min
Pressure 7.154Mpascalls
The wavelength used in HPLC may be approximately 214 nm.

Modified albumin may elute between 39–44 minutes (FIG. 5). Albumin fragments may elute much earlier, mainly at less than 20 minutes.

The method for determining the propensity for kidney disease is applicable to any individual. Kidney disease may be caused by a number of factors including bacterial infection, allergic, congenital defects, stones, tumors, chemicals or from diabetes. Preferably, the method is applicable for determining a propensity for kidney disease in diabetic patients that may progress to a kidney disease. Preferably, the individual is a normoalbuminuric diabetic. However, normal individuals may be monitored for propensity for the disease by determining increased levels of intact or modified albumin in the urine.

The method of the invention can be carried out using non-antibody separation procedures as described above. However, antibody specific for modified protein may also be used to detect the presence of the modified protein.

The antibody to the modified protein may be obtained using the following method. The procedure is described specifically for albumin by way of example only, and can be readily applied to antibody production against any other protein in the urine. The method seeks to determine which modified albumin molecule is the most sensitive marker to identify diabetic patients, for example, who will progress to kidney complications.

The modified albumin is characterized by carrying out a quantitative separation of the modified albumin molecules, such as by preparative HPLC. The modified proteins are analyzed for ligand binding, such as glycation. Subsequently, amino acid sequence of the individual modified protein is determined, preferably by mass spectrometry using methods described in Karger B L, Hancock WS (eds.) *High Resolution Separation and Analysis of biological Macromolecules. Part A Fundamentals in Methods in Enzymology,* Vol. 270, 1996, Academic Press, San Diego, Calif., USA; or Karger B L, Hancock W S (eds.) *High Resolution Separation and Analysis of biological Macromolecules. Part B Applications in Methods in Enzymology,* Vol. 271, 1996, Academic Press, San Diego, Calif., USA, for example, which references are incorporated herein by reference in their entirety. In a preferred embodiment, there may be about 3 to 4 modified albumin species.

The method of generating antibody against the modified albumin seeks to develop a diagnostic immunoassay for the modified albumin that predicts those diabetic patients, for example, that progress to kidney complications. To accomplish this, sufficient quantities of modified albumin is prepared by HPLC. Antibodies are made by sequential injection of the modified albumin in an animal such as a rabbit, to generate good titer, and the antibodies are isolated using conventional techniques using methods described in Goding J W, Monoclonal Antibodies: Principles and Practice. *Production and Application of Monoclonal Antibodies in Cell Biology, Biochemistry and Immunology,* 2nd Edition 1986, Academic Press, London, UK; or Johnstone A, Thorpe R, *Immunochemistry in Practice,* 3rd edition 1996, Blackwell Science Ltd, Oxford, UK, for example, which references are incorporated herein by reference in their entirety. The obtained antibodies may be polyclonal antibodies or monoclonal antibodies.

Preferably, at least one species of a modified albumin is isolated and identified for use in determining a propensity for kidney disease. The isolated species may be used to generate antibodies for use in immunoassays. The antibodies may be tagged with an enzymatic, radioactive, fluorescent or chemiluminescent label. The detection method may include, but is not limited to radioimmuoassay, immunoradiometric assay, fluorescent immunoassay, enzyme linked immunoassay, and protein A immunoassay. The assays may be carried out in the manner described in Goding J W, *Monoclonal Antibodies: Principles and Practice. Production and Application of Monoclonal Antibodies in Cell Biology, Biochemistry and Immunology.* 2nd Edition 1986, Academic Press, London, UK; Johnstone A, Thorpe R, *Immunochemistry in Practice,* 3rd edition 1996, Blackwell Science Ltd, Oxford, UK; or Price C P, Newman D J (eds.) *Principles and Practice of Immunoassay,* 2nd Edition, 1997 Stockton Press, New York, N.Y., USA, for example, which references are incorporated herein by reference in their entirety.

It is an object of this invention to provide an article of matter or a kit for rapidly and accurately determining the presence or absence of modified protein such as modified albumin, in a sample quantitatively or non-quantitatively as desired. Each component of the kit(s) may be individually packaged in its own suitable container. The individual container may also be labeled in a manner, which identifies the contents. Moreover, the individually packaged components may be placed in a larger container capable of holding all desired components. Associated with the kit may be instructions, which explain how to use the kit. These instructions may be written on or attached to the kit.

The invention is also directed to a method of determining a treatment agent for renal disease and/or renal complications of a disease, comprising:

(a) administering to a person an agent that is suspected of being able to treat the disease;

(b) obtaining a urine sample from the person; and (c) assaying for the modified form of the protein in the sample, wherein either the presence of or lack of presence of a modified form of the protein in the urine or decreasing amount of the modified form of the protein over time indicates that the agent is a treatment agent for the disease. The treatment agent may be a lysosome activating agent that may act directly or indirectly to activate lysosome, and thereby cause the lysosome to digest post-glomerular filtered proteins, which is a sign of a healthy kidney.

The process of trafficking of proteins to the lysosomes plays a role in the mechanism of albuminuria in diabetes. An intracellular molecule that is involved in trafficking is protein kinase C (PKC). It is contemplated that a drug or agent can be formulated that will activate lysosomal trafficking or inhibit PKC.

Accordingly, in one aspect of the present invention, there is provided a lysosome-activating compound for use in reactivating lysosomes or processes that direct substrates to the lysosome or products away from the lysosome.

In another aspect of the present invention, there is provided a composition comprising a lysosome-activating compound and a carrier.

In yet another aspect of the invention there is provided a method of preventing or treating kidney disease, said method including administering an effective amount of a lysosome-activating compound to a subject.

In yet another aspect of the present invention, there is provided a method of screening a multiplicity of compounds to identify a compound capable of activating lysosomes or processes that direct substrates to the lysosome or products away from the lysosome, said method including the steps of:

(a) exposing said compound to a lysosome and assaying said compound for the ability to activate a lysosome wherein said lysosome when activated has a changed activity;

(b) assaying for the ability to restore a cellular process to substantially normal levels in kidney tissue, wherein said kidney tissue has a low lysosome activity; and/or (c) assaying for the ability to restore tissue turnover to substantially normal levels in kidney tissue, wherein said kidney tissue has low lysosome activity.

Lysosomes may be associated with the breakdown of proteins, particularly albumin, in the kidney. In cases of microalbuminuria, substantial amounts of albumin escape lysosomal breakdown possibly due to a deactivated lysosome. Restoration of lysosomal breakdown may restore the balance in the kidney of cellular processes and tissue turnover.

A lysosome-activating compound may be a compound that acts directly or indirectly on the lysosome. By acting indirectly, the compound may act on a component, which influences the activity of the lysosome. Nevertheless, the outcome results in an activation of the lysosome, thereby providing enhanced protein breakdown.

In another aspect of the present invention, there is provided a composition comprising a lysosome-activating compound and a carrier.

The composition may be a physiologically acceptable or pharmaceutically acceptable composition. However, it will be a composition which allows for stable storage of the lysosome activating compound. Where the composition is a pharmaceutically acceptable composition, it may be suitable for use in a method of preventing or treating kidney disease.

In yet another aspect of the invention there is provided a method of preventing or treating kidney disease, said method including administering an effective amount of a lysosome-activating compound to a subject.

As described above, the lysosome-activating compound may act by reactivating the lysosome so that cellular processes and tissue turnover are restored fully or in part, thereby resulting in the kidney being restored partially or fully. In any case, administering a lysosome activating compound to an animal having kidney disease may restore lysosome activity fully or in part.

Methods of administering may be oral or parenteral. Oral may include administering with tablets, capsules, powders, syrups, etc. Parenteral administration may include intravenous, intramuscular, subcutaneous or intraperitoneal routes.

The changed activity of the lysosome is preferably a change which enhances the activity of the lysosome so that albumin breakdown is improved. The ability to not only activate lysosome but also improve cellular processes and/or tissue turnover is a characteristic of the most desirable lysosome activating compound. Preferably, it is desired to use the lysosome activating compound to restore kidney function.

In another aspect of the present invention there is provided a method for preventing kidney disease in a subject, said method including:

(a) measuring the amount of intact and modified intact albumin content in a urine sample;

(b) determining a change in the amount of intact albumin in the urine that has been modified so as to be not detectable by conventional RIA methods wherein the change is indicative of a propensity for kidney disease; and treating the animal for a kidney disease when a change is determined.

The following examples are offered by way of illustration of the present invention, and not by way of limitation.

EXAMPLES

Example 1

Size Exclusion Chromatography of Human Serum Albumin (HSA)

Normal, healthy volunteers were used to provide urine for analyzing the distribution of albumin in their urine.

$^3$H[HSA] (Human Serum Albumin) was injected into healthy volunteers and urine and plasma were collected and analyzed by size exclusion chromatography using a G-100 column. The column was eluted with PBS (pH=7.4) at 20 ml/hr at 4° C. The void volume ($V_o$) of the column was determined with blue dextran T2000 and the total volume with tritiated water.

Tritium radioactivity was determined in 1 ml aqueous samples with 3 ml scintillant and measured on a Wallac 1410 liquid scintillation counter (Wallac Turku, Finland).

Figure 1:
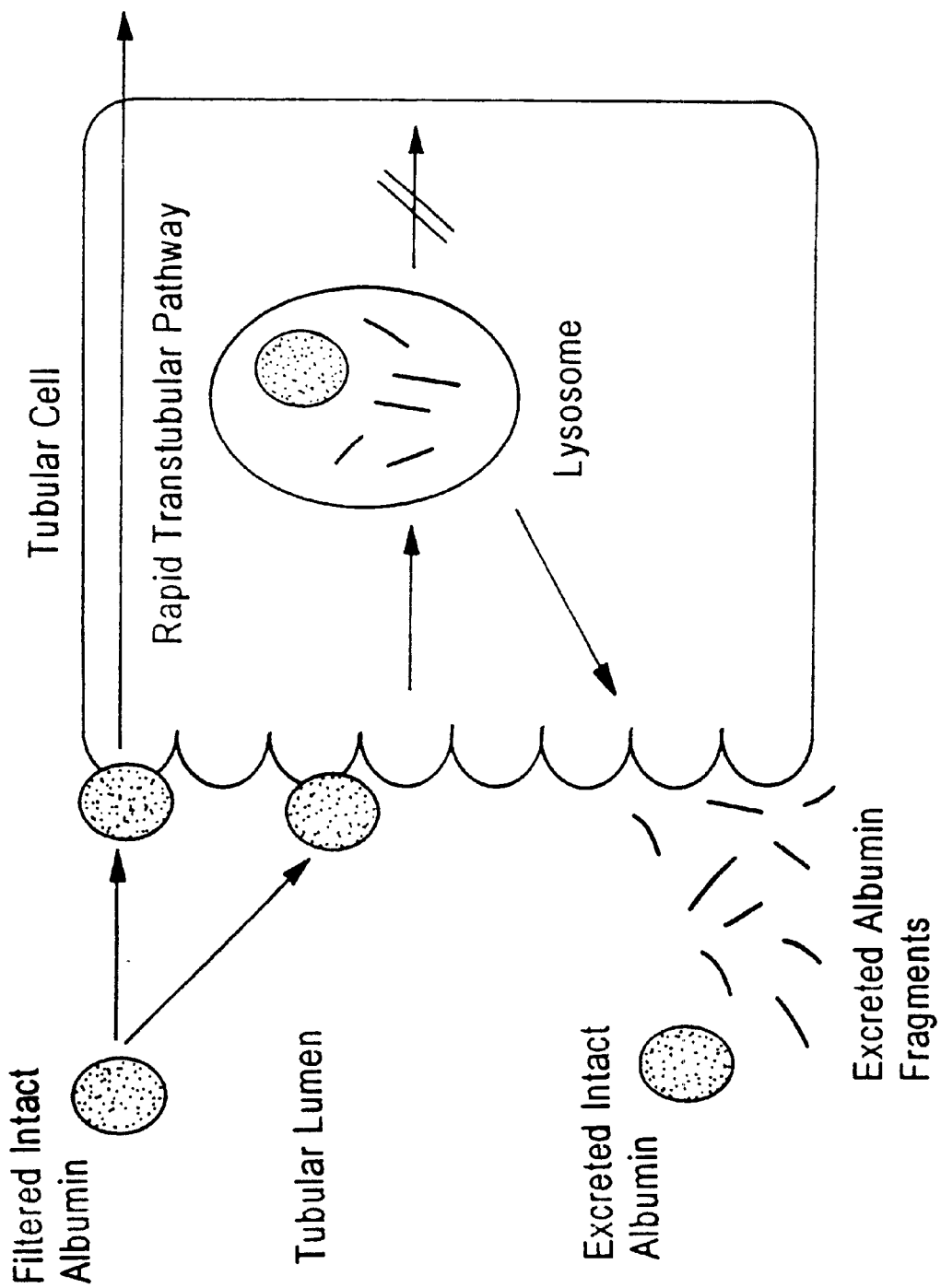
FIG. 1 illustrates the progress of filtered intact albumin into tubular cells and breakdown of albumin to provide excreted albumin fragments.
Figure 2:
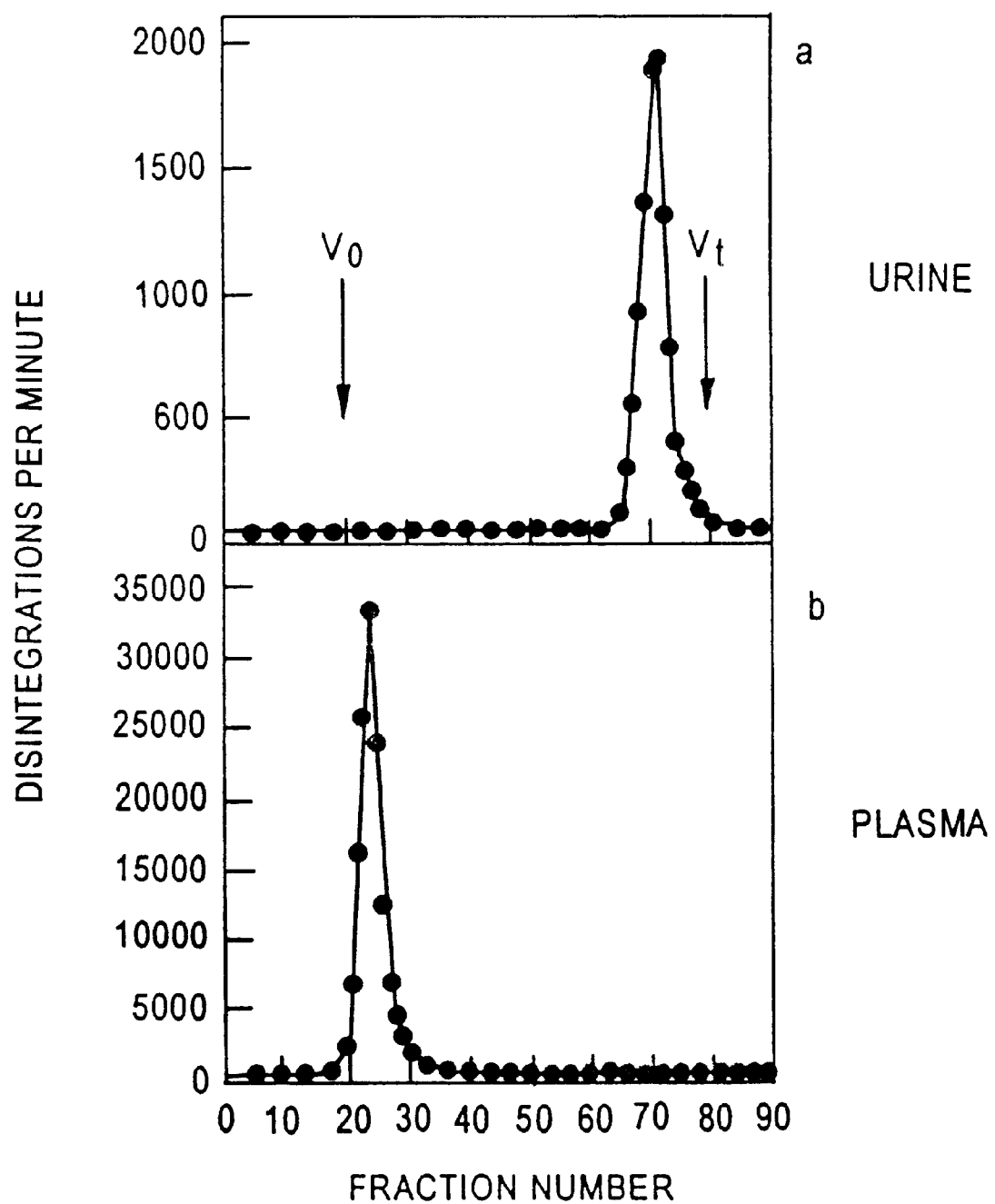
FIGS. 2a and 2b illustrate a representative profile of ($^3$H) HSA in (a) urine and (b) plasma collected from normal, healthy volunteers by size exclusion chromatography. Urine contains mostly fragmented albumin. And plasma contains mostly intact albumin.

FIG. 2 illustrates the distribution of albumin in urine and in plasma.

Example 2

Albumin Excretion in a Normal Healthy Volunteer and Diabetic Patient $^3$H[HSA] as used in Example 1 was injected into a normal, healthy volunteer and a diabetic patient. Samples of urine were collected and $^3$H[HSA] was determined as in Example 1.

Figure 3:
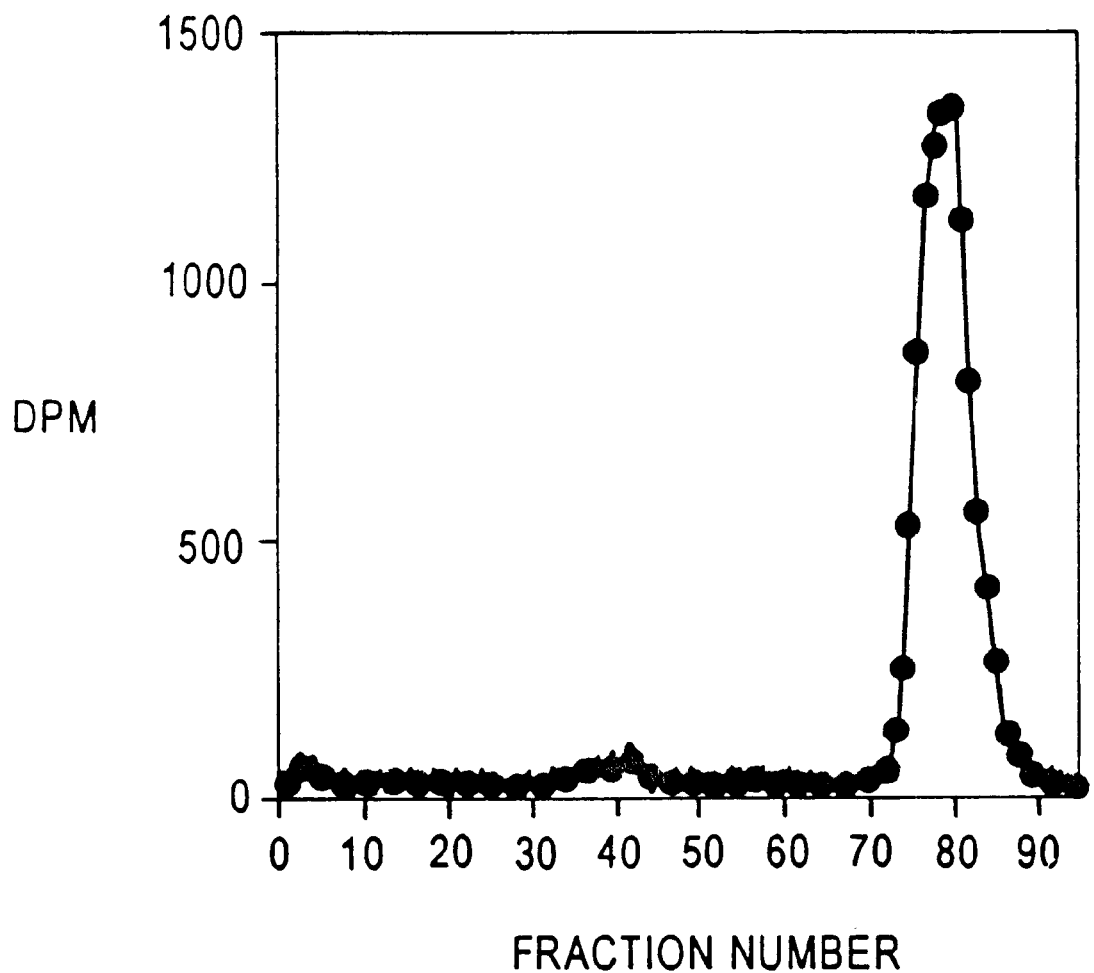
FIG. 3 illustrates urine from normal, healthy volunteer showing a fragmented albumin peak, but no intact albumin peak from size exclusion chromatography.

The normal, healthy volunteer (FIG. 3) shows the excretion of fragments of albumin on a size exclusion chromatography as performed in Example 1.

Figure 4:
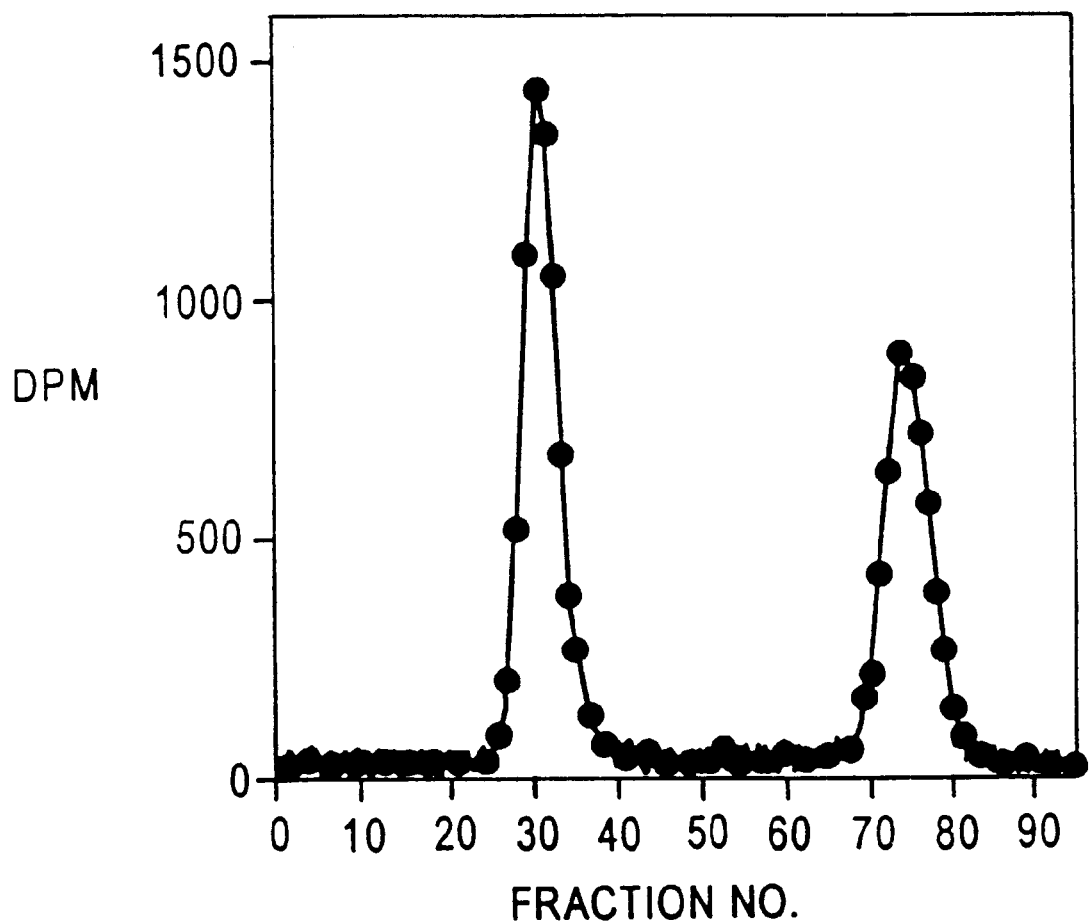
FIG. 4 illustrates urine from a diabetic patient showing both intact and fragmented albumin peaks from size exclusion chromatography.

The diabetic patient (FIG. 4) shows the presence of substantially full-length and fragmented albumin on size exclusion chromatography. However, excretion rates of albumin detectable by these methods were in the order of 5 μg/min (control) and 1457 μg/min (diabetic).

Example 3

Determination of Intact Albumin, and Intact/Modified Albumin on HPLC.

Urine samples were collected from normal, healthy volunteer, normoalbuminuric diabetic patients and from macroalbuminuric patients. Urine was collected midstream in 50 ml urine specimen containers. The urine was frozen until further use. Prior to HPLC analysis the urine was centrifuged at 5000 g.

Samples were analyzed on HPLC using a hydrophobicity column Zorbax 300 SB-CB (4.6 mm×150 mm). A 50 μl sample loop was used.

Samples were eluted from the columns using the following conditions.

Solvent A H₂O, 1% trifluoro acetic acid
Solvent B 60% acetonitrile, 0.09% TFA
Solvent A2 99.96>00.00:49.58 min
Pressure 9.014Mpascalls (~1100 psi)
Solvent B2 0.04>100.0:49.58 min
Pressure 7.154Mpascalls
A wavelength of 214 nm was used.

Example 4

Purification of Modified Albumin for Antibody Production by Standard Techniques

Urine from microalbuminuric patient which had an intact albumin concentration of 43.5 mg/L as determined by turbitimer (involving conventional immunochemical assay) was initially filtered through a 30 kDa membrane to separate the modified albumin from low molecular weight (<30,000) protein fragments in urine. The material that was retained by the filter gave a yield of intact albumin of 27.4 mg/L as determined by turbitimer assay. This retained material was then subjected to size exclusion chromatography on Sephadex G100. The material collected was the peak fraction that coelutes with intact albumin. This material gave a yield of 15.2 ml/L of albumin as determined by the turbitimer method. This material was then subjected to affinity chromatography on an intact albumin antibody column. This column will only bind albumin that has conventional epitopes. The yield of material that eluted from the column was <6 mg/L (lowest sensitivity of the turbitimer). This is expected as the immunoreactive albumin would have bound to the affinity column. The eluate was then subject to reverse phase HPLC chromatography (as described above) to determine the amount of immuno-unreactive albumin in the sample. A 1452 unit area corresponding to 30.91 mg/L of purified modified albumin was noted as shown in FIG. 5. This purified modified albumin can then be used for antibody production by standard means.

Results

FIG. 5 illustrates a HPLC profile of albumin alone. Essentially a single peak which elutes at approximately 39–44 minutes retention time was obtained.

Figure 6:
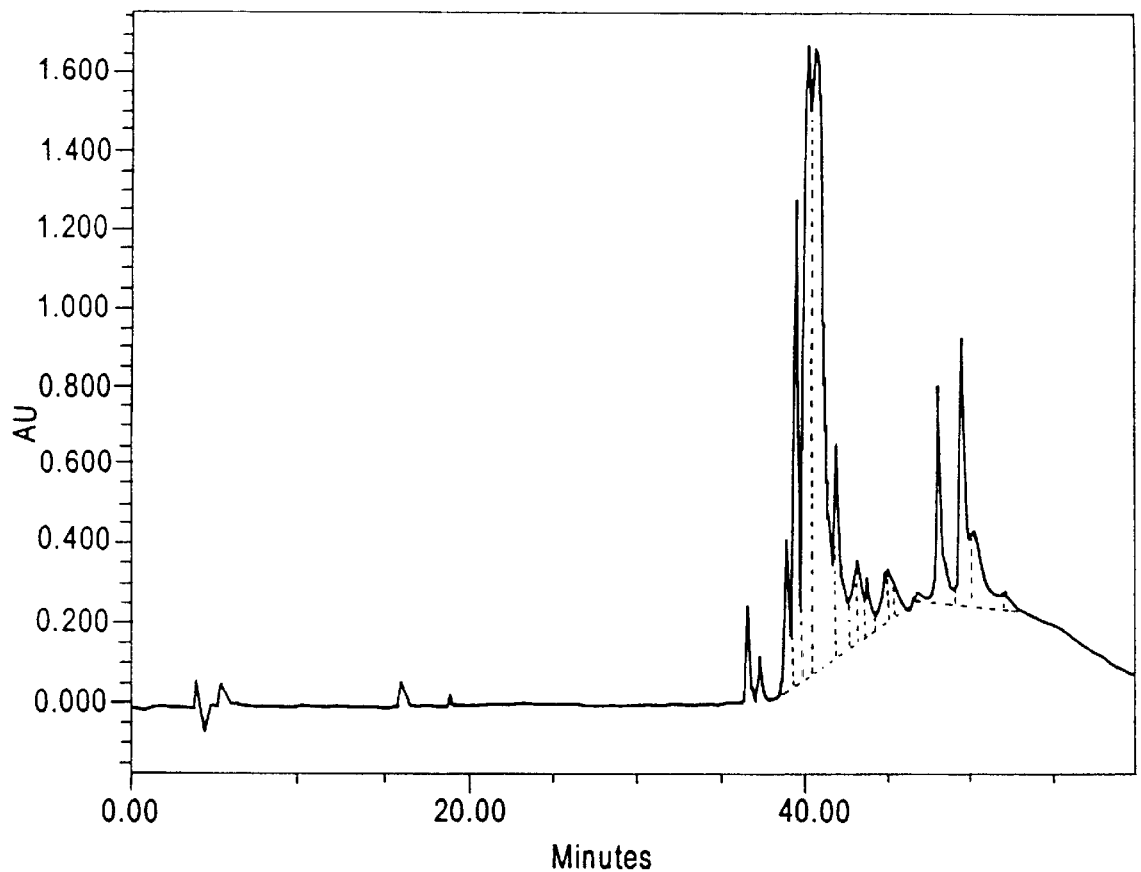
FIG. 6 illustrates the HPLC profile of plasma from normal, healthy volunteer showing albumin peaks.

FIG. 6 illustrates a HPLC profile of plasma showing a distinct albumin peak at approximately 39–44 minutes as well as other peaks corresponding to other plasma proteins.

Figure 7:
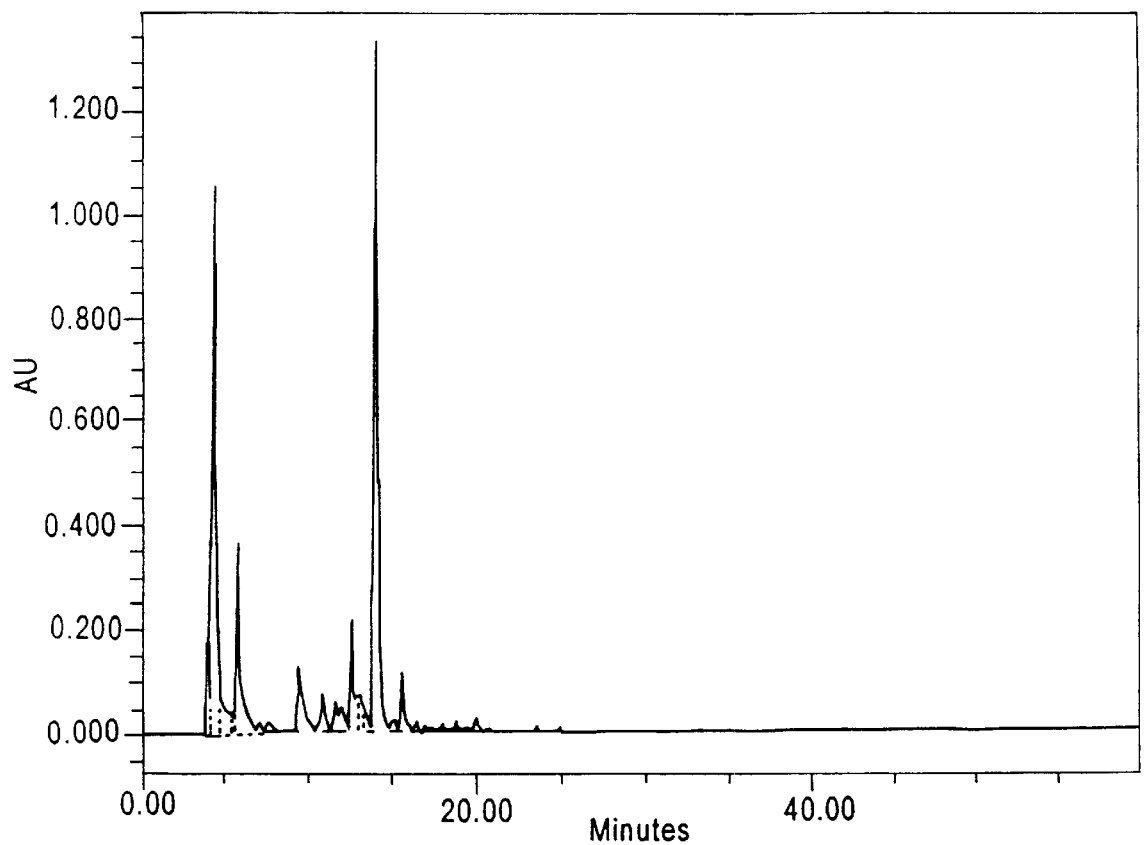
FIG. 7 shows the HPLC profile of urine from normal, healthy volunteer with fragmented products of albumin but no intact albumin peak.

FIG. 7 illustrates a HPLC profile of a normal, healthy volunteer showing no albumin peak in the urine sample. This individual breaks down the albumin excreted into the urine possibly via an active lysosome. Substantial fragmented products were evident showing prominence of some species, particularly of a species at approximately less than 14.5 minutes retention time.

Figure 8:
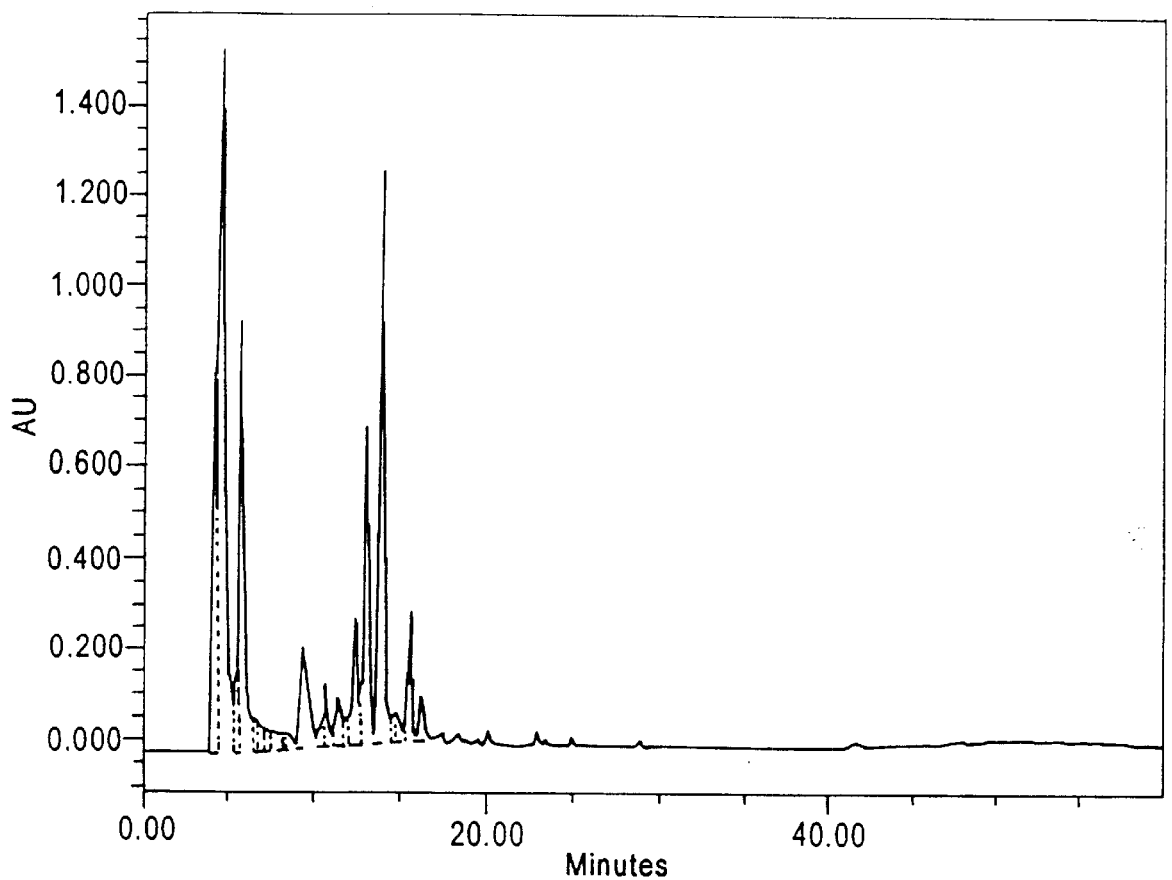
FIG. 8 shows the HPLC profile of a urine sample from a normoalbuminuric diabetic patient showing albumin breakdown products and a small-modified albumin peak at approximately 39–44 minutes retention time.

When urine from a normoalbuminuric diabetic patient (with an albumin excretion rate of 8.07 μg/min, as measured by RIA) is analyzed (FIG. 8), small amounts of modified albumin eluting at approximately 39–44 minutes retention time is evident. Whereas conventional test indicates the presence of <6 mg/l of albumin in the urine sample, the method of the invention showed that the true albumin content in the urine sample was 26.7 mg/l. Treatment for the disease should have begun on this individual. Albumin by-products or fragmented albumin is present as in the normal, healthy volunteer.

Figure 9:
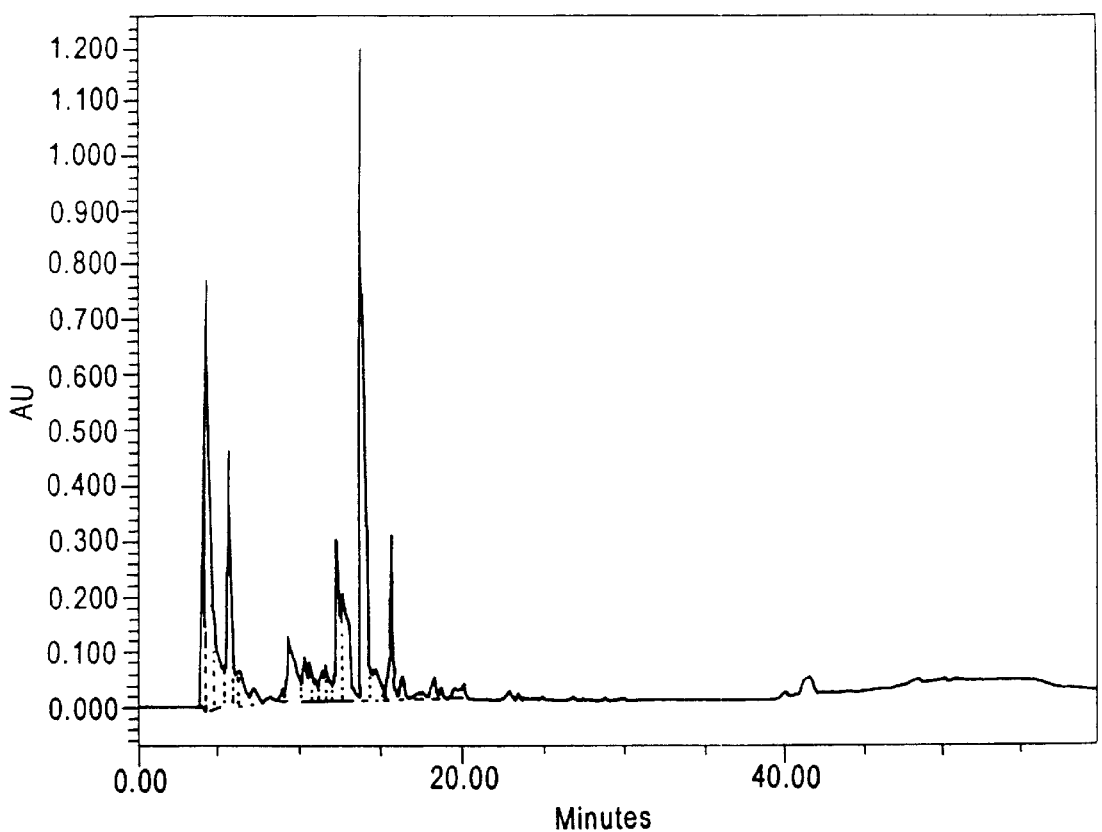
FIG. 9 shows the HPLC profile of urine from a normoalbuminuric diabetic patient showing signs of kidney failure and the presence of the characteristic spiked albumin peak at approximately 39–44 minutes retention time.

Another urine sample from normoalbuminuric diabetic patient (with albumin excretion rate of 17.04 μg/min) was analyzed (FIG. 9). RIA tests show albumin excreted in the urine for this patient. However, on HPLC (FIG. 9) an albumin or modified albumin peak is evident at approximately 39–44 minutes retention time. Whereas conventional test indicates the presence of <6 mg/l of albumin in the urine sample, the method of the invention showed that the true albumin content in the urine sample was 81.3 mg/l. Treatment for the disease should have begun on this individual. This peak begins to show a multiple peaked appearance. A smaller peak corresponding to intact albumin shows that modified albumin may represent the peak at 39–44 minutes. The presence of this albumin peak compared with the profile of a normal, healthy volunteer having no albumin peak shows a change in the detectable levels of the amount of intact/modified albumin. This may signal a propensity for a kidney disease.

Figure 10:
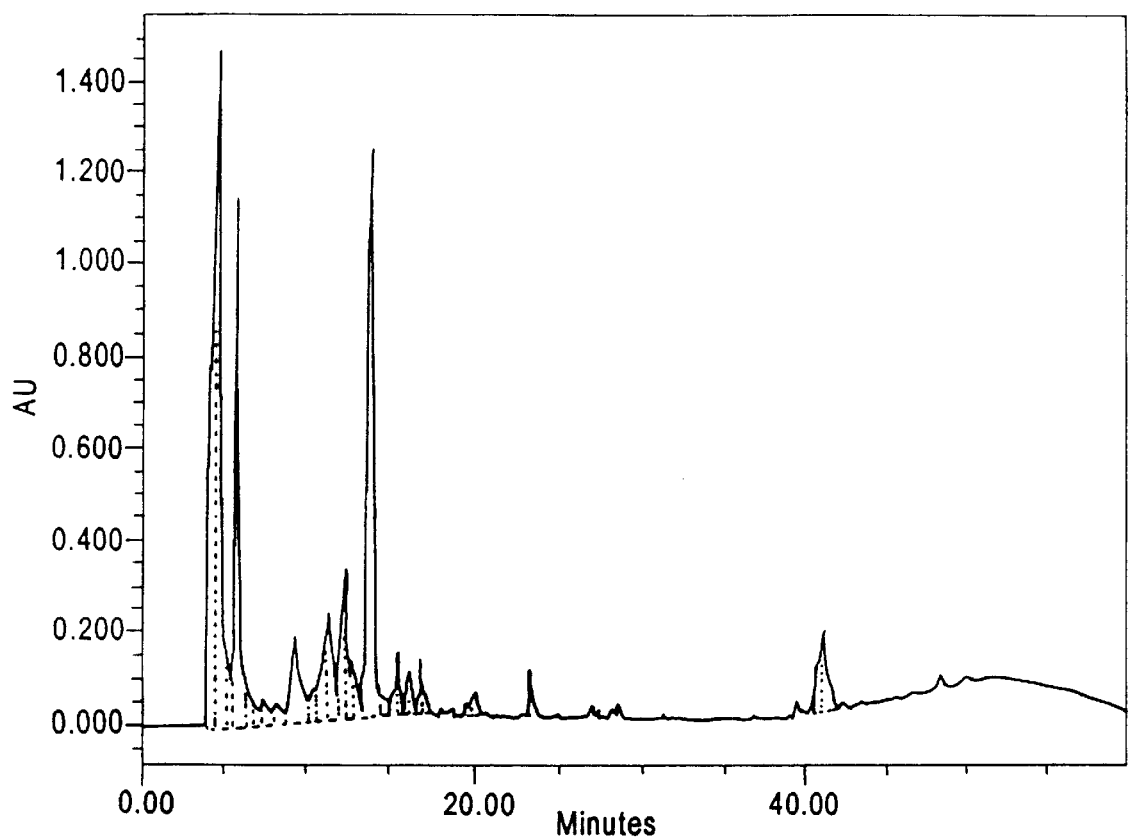
FIG. 10 illustrates a HPLC profile of a normoalbuminuric diabetic patient showing signs of kidney failure and the presence of the characteristic spiked modified albumin peak at approximately 39–44 minutes retention time.

A further urine sample from a normoalbuminuric diabetic patient (with an albumin excretion rate of 4.37 μg/min) was analyzed, and the HPLC profile is illustrated in FIG. 10. Again, modified albumin was detected at approximately 39–44 minutes retention time showing multiple peaks. This patient again did register normal albumin by RIA. Whereas conventional test indicates the presence of <6 mg/l of albumin in the urine sample, the method of the invention showed that the true albumin content in the urine sample was 491 mg/l. Treatment for the disease should have begun on this individual. It is clear that modified albumin assessment is necessary to identify these changes. This patient would be determined to have a propensity for kidney disease. As kidney disease progresses, the modified albumin peak will continue to increase.

Figure 11:
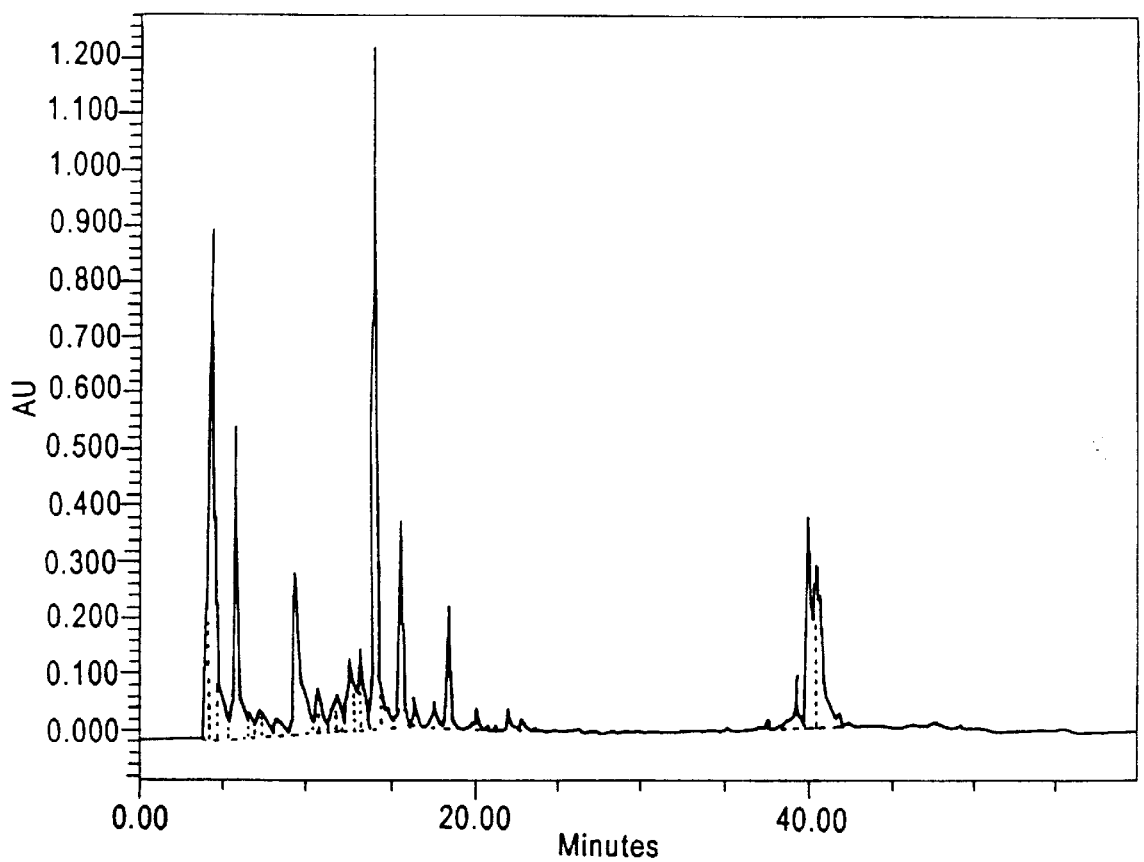
FIG. 11 illustrates a HPLC of a macroalbuminuric diabetic patient showing high levels of the normal albumin as well as the characteristic spiked appearance at approximately 39–44 minutes retention time.

This is shown in FIG. 11 where a urine sample of a macroalbuminuric patient was analyzed. A quite significant albumin peak at approximately 39–44 minutes retention time showing multiple peaks was evident. The patient's albumin content was 1796 mg/l. Treatment for this individual is in progress.

Figure 12:
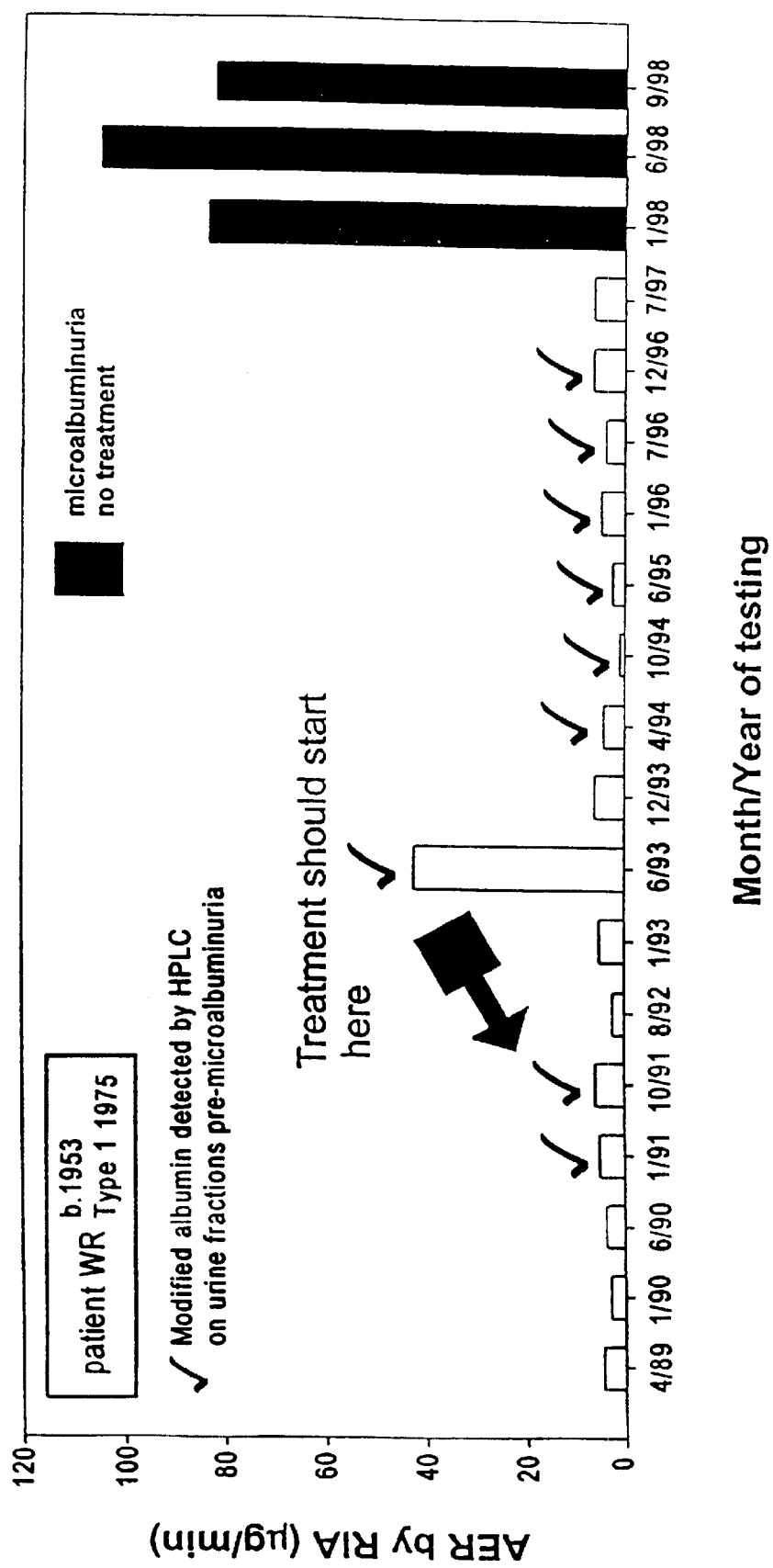
FIG. 12 illustrates a longitudinal study of a patient in which the modified protein was detected at a time prior to onset of diabetic nephropathy, indicating predisposition to diabetic nephropathy, and the delay in treatment caused by relying on conventional RIA methods.
Figure 13:
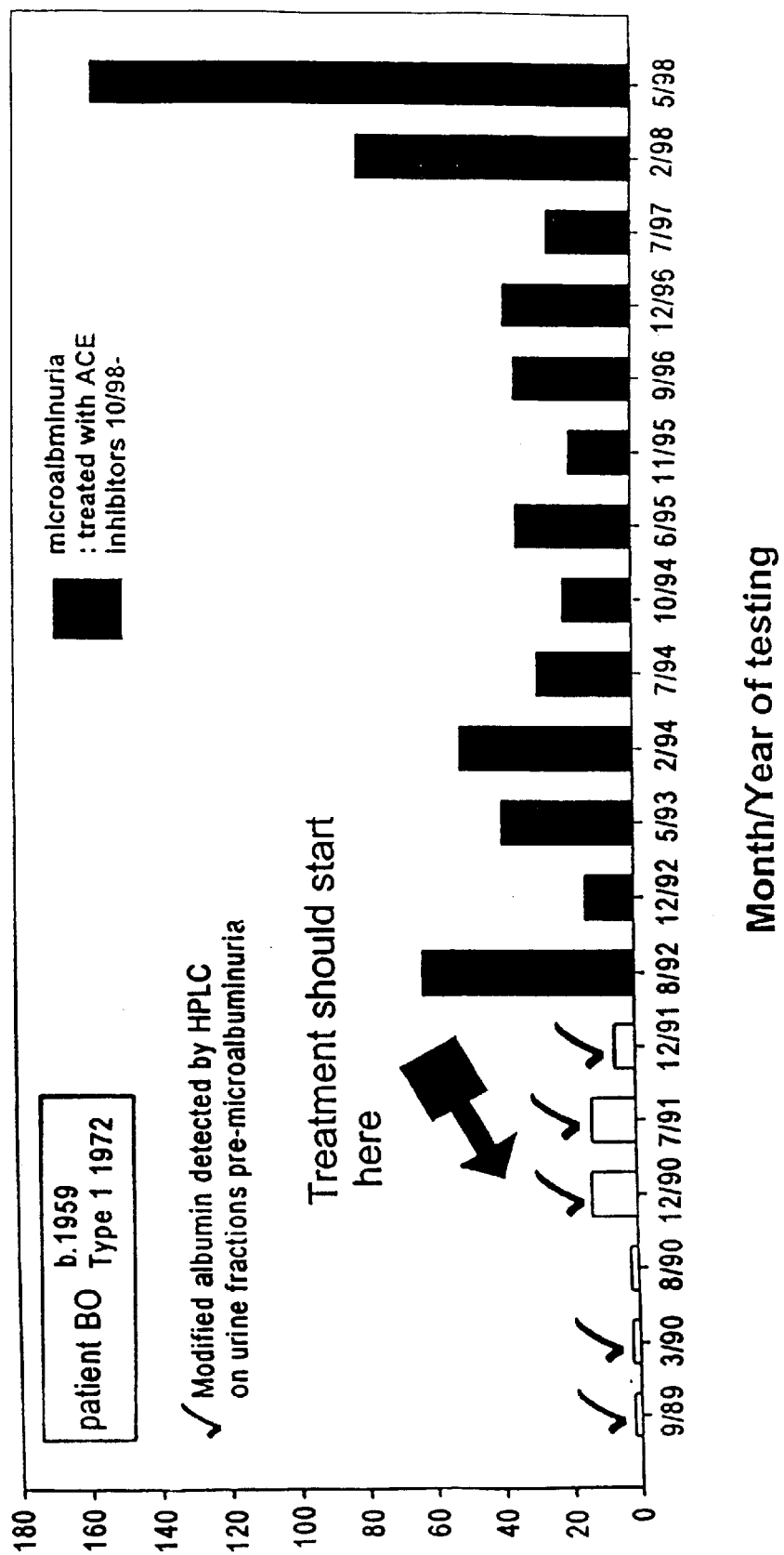
FIG. 13 illustrates a longitudinal study of a patient in which the modified protein was detected at a time prior to onset of diabetic nephropathy, indicating predisposition to diabetic nephropathy, and the delay in treatment caused by relying on conventional RIA methods.
Figure 14:
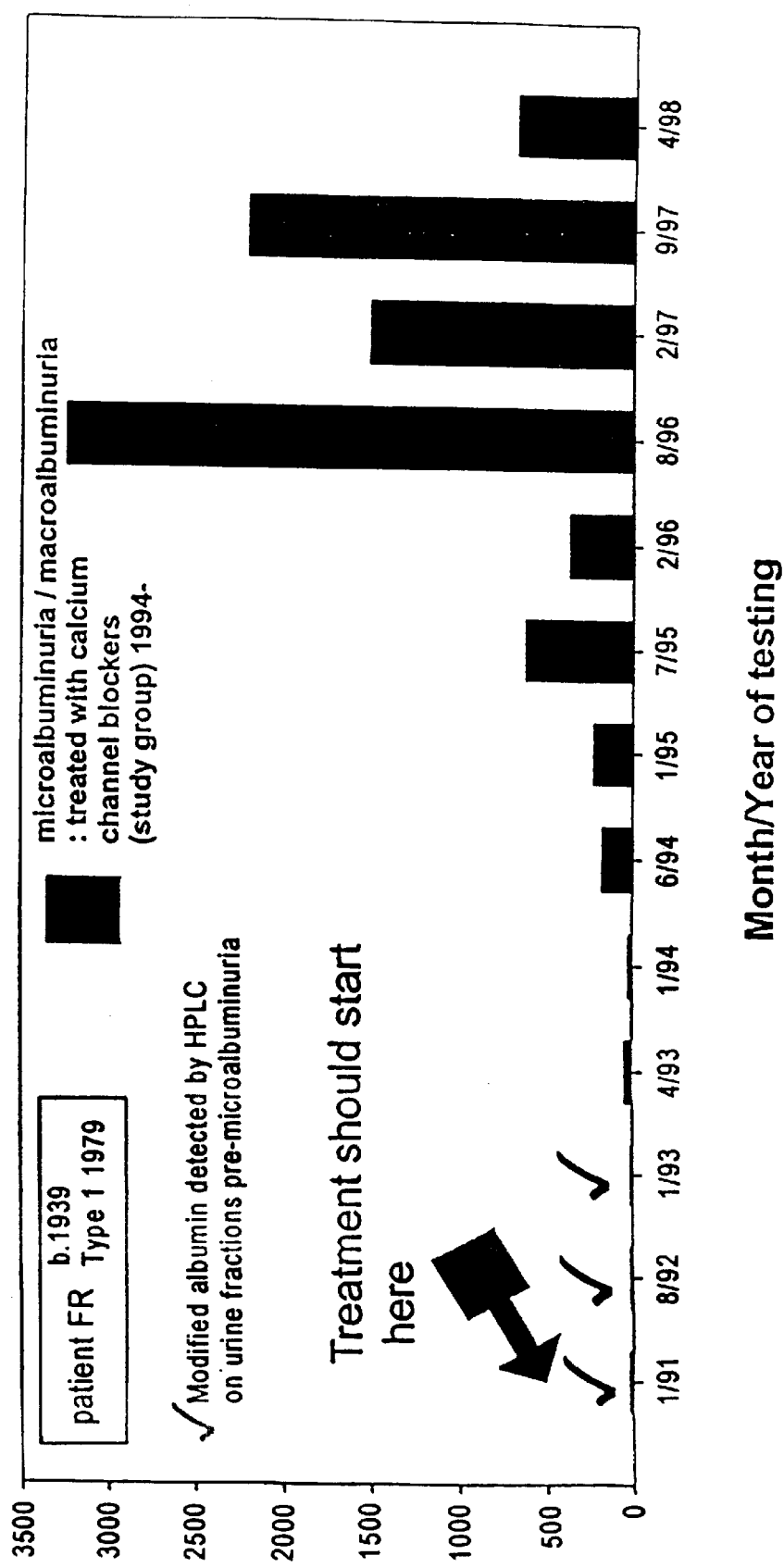
FIG. 14 illustrates a longitudinal study of a patient in which the modified protein was detected at a time prior to onset of diabetic nephropathy, indicating predisposition to diabetic nephropathy, and the delay in treatment caused by relying on conventional RIA methods.
Figure 15:
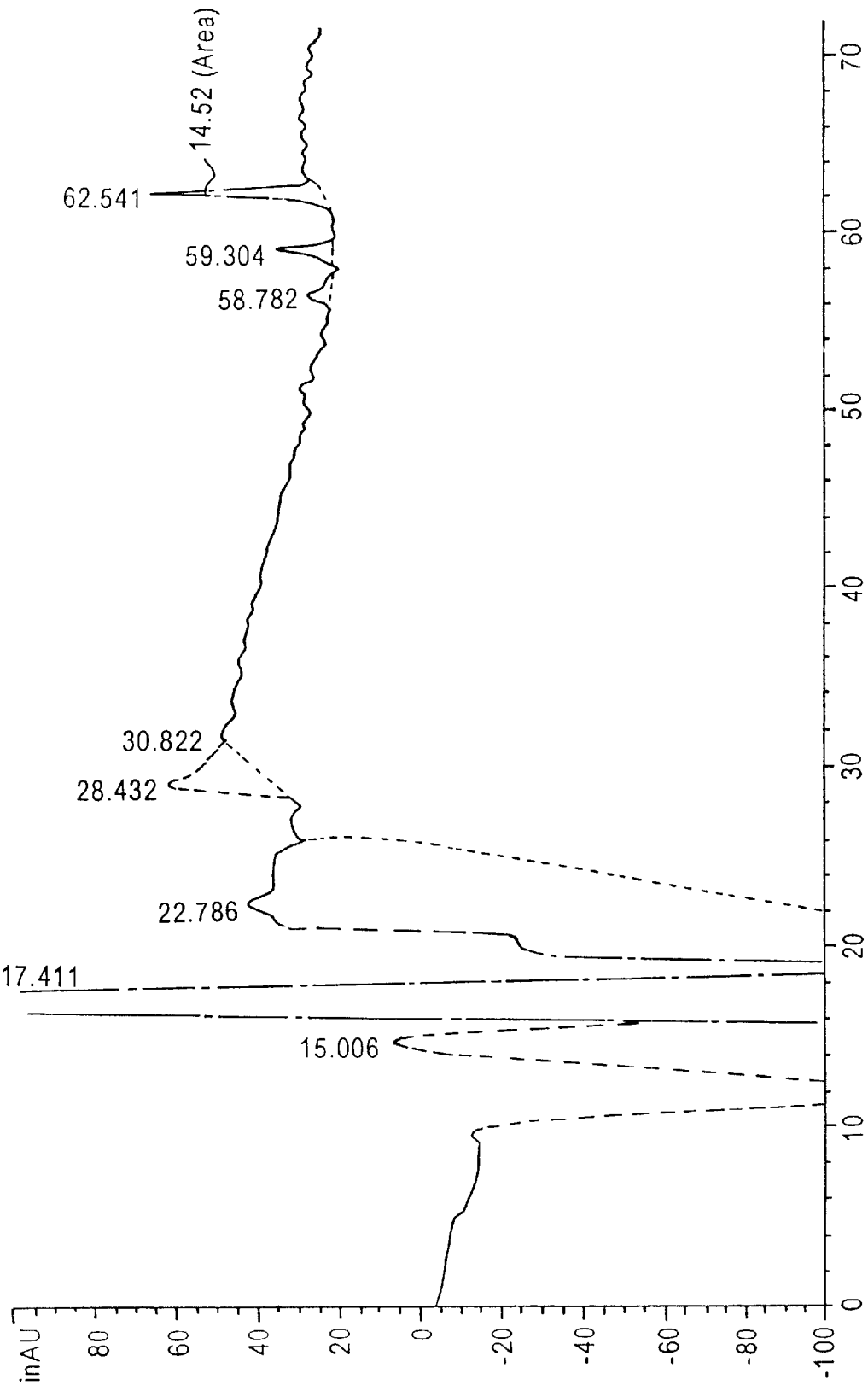
FIG. 15 shows the HPLC chromatogram used as a criterion of purity of the modified albumin of Example 4.

The method of the invention results in early detection of a propensity for a renal disease as illustrated by the longitudinal studies in FIGS. 12–14. FIGS. 12–14 show situations in which the ACE inhibitor treatment for diabetes was begun later than it should have had the modified albumin detection method of the invention been used. Detecting modified protein using the method according to the invention is a more effective method for predicting the onset of a renal disease than using conventional RIA.

All of the references cited herein are incorporated by reference in their entirety.

Finally, it is to be understood that various other modifications and/or alterations may be made without departing from the spirit of the present invention as outlined herein.

What is claimed is:

1. A method for measuring albumin content in a urine sample, comprising assaying the urine sample for albumin by conventional assay and assaying for intact modified albumin.

2. The method according to claim 1, wherein said conventional assay comprises an antibody method or fractionating said sample via chromatography, electrophoresis or sedimentation to test for native and/or intact modified albumin.

3. The method according to claim 1, wherein assaying for intact modified albumin comprises fractionating said sample via chromatography, electrophoresis or sedimentation, or use of a specific albumin dye method to test for native and/or intact modified albumin in said urine sample.

4. A method for detecting protein content in a urine sample by non-antibody assay, comprising detecting a sum of native protein and intact modified protein in the urine sample.

5. The method according to claim 4, wherein said non-antibody assay comprises fractionating the protein in said sample via chromatography, electrophoresis or sedimentation to test for the presence of native and/or intact modified protein.

6. A method for diagnosing kidney disease or renal complications of disease prior to the onset of kidney degeneration in a patient by detecting protein content in a urine sample obtained from the patient, comprising detecting intact modified protein and native protein amount in the sample by non-antibody assay; and correlating the presence of native and/or intact modified protein in the urine to the presence of kidney disease or renal complications of disease.

7. The method according to claim 6, wherein said non-antibody assay comprises fractionating the protein in said sample via chromatography, electrophoresis or sedimentation to test for the presence of native protein and/or intact modified protein.

8. The method according to claim 6, wherein said protein is albumin.

9. The method according to claim 6, wherein the disease comprises nephropathy, diabetes insipidus, diabetes type I, diabetes II, renal disease glomerulonephritis, bacterial or viral glomerulonephritides, IgA nephropathy, Henoch-Schönlein Purpura, membranoproliferative glomerulonephritis, membranous nephropathy, Sjögren's syndrome, nephrotic syndrome minimal change disease, focal glomerulosclerosis and related disorders, acute renal failure, acute tubulointerstitial nephritis, pyelonephritis, GU tract inflammatory disease, Pre-clampsia, renal graft rejection, leprosy, reflux nephropathy, nephrolithiasis, genetic renal disease, medullary cystic, medullar sponge, polycystic kidney disease, autosomal dominant polycystic kidney disease, autosomal recessive polycystic kidney disease, tuborous sclerosis, von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies, monoclonal gammopathies, multiple myeloma, amyloidosis and related disorders, febrile illness, familial Mediterranean fever, HIV infection—AIDS, inflammatory disease, systemic vasculitides, polyarteritis nodosa, Wegener's granulomatosis, polyarteritis, necrotizing and crecentic glomerulonephritis, polymyositis-dermatomyositis, pancreatitis, rheumatoid arthritis, systemic lupus erythematosus, gout, blood disorders, sickle cell disease, thrombotic thrombocytopenia purpura, hemolytic-uremic syndrome, acute corticol necrosis, renal thromboembolism, trauma and surgery, extensive injury, burns, abdominal and vascular surgery, induction of anesthesia, side effect of use of drugs or drug abuse, malignant disease, adenocarcinoma, melanoma, lymphoreticular, multiple myeloma, circulatory disease myocardial infarction, cardiac failure, peripheral vascular disease, hypertension, coronary heart disease, non-atherosclerotic cardiovascular disease, atherosclerotic cardiovascular disease, skin disease, soriasis, systemic sclerosis, respiratory disease, COPD, obstructive sleep apnoea, hypoia at high altitude or erdocrine disease, acromegaly, diabetes mellitus, or diabetes insipidus.

10. The method according to claim 6, wherein the protein comprises albumin, globulin, $\alpha_1$-globulin, $\alpha_2$-globulin, $\beta$-globulin, $\gamma$-globulin, euglobulin, pseudoglobulin I or II, fibrinogen, $\alpha_1$-acid glycoprotein, $\alpha_1$-glycoprotein, $\alpha_1$-lipoprotein, ceruloplasmin, $\alpha_2$ 19S glycoprotein, $\beta_1$ transferrin, $\beta_1$ lipoprotein, immunoglobulins A, E, G, or M, horseradish peroxidase, lactate dehydrogenase, glucose oxidase, myoglobin, lysozyme, protein hormone, growth hormone, insulin or parathyroid hormone.

11. The method according to claim 7, wherein the protein is albumin.

12. The method according to claim 7, wherein said non-antibody assay comprises partition chromatography, adsorption chromatography, paper chromatography, thin-layer chromatography, gas-liquid chromatography, gel chromatography, ion-exchange chromatography, affinity chromatography, or hydrophobic interaction chromatography, moving-boundary electrophoresis, zone electrophoresis, or isoelectric focusing.

13. The method according to claim 12, wherein the non-antibody assay is hydrophobic interaction chromatography carried out in a high pressure liquid chromatography (HPLC) apparatus.

14. A method for detecting renal disease caused by diabetes comprising:
 i) collecting a series of urine samples from a patient over a period of time,
 ii) subjecting each urine sample in the series of samples to analysis by chromatography, electrophoresis, sedimentation, or antibody assay,
 iii) detecting an increase in the sum of native protein and/or intact modified protein in the samples over the period of time, wherein an increase in the amount of the intact modified protein and native protein or intact modified protein is indicative of the presence of the renal disease.

15. A method for detecting renal disease caused by diabetes by the steps comprising:
 i) collecting a urine sample from a person,
 ii) subjecting the urine sample to analysis by chromatography, electrophoresis, sedimentation apparatus, or antibody means; and
 iii) detecting the presence of intact modified albumin in the sample, wherein the presence of the intact modified albumin in indicative of the presence of the renal disease.

16. The method according to claim 14, wherein the modified protein is detected by an antibody that is specific for native and/or intact modified forms of the protein.

17. The method according to claim 16, wherein the antibody is specific for the modified protein.

18. The method according to claim 14, wherein the antibody is attached to an enzymatic, radioactive, fluorescent or chemiluminescent label, wherein the detecting step comprises radioimmunoassay, immunoradiometric assay, fluorescent immunoassay, enzyme linked immunoassay, or protein A immunoassay.

19. The method according to claim 14, wherein an early stage of the disease prior to the onset of kidney degeneration is diagnosed when the intact modified protein is present in the urine in increasing amounts over time.

20. An article of manufacture for diagnosing early stage of a disease in which intact modified protein found in urine is an indicator of the disease, comprising:
 (a) a container comprising a labeled antibody specific for said modified protein;
 (b) a container comprising reagents for developing an antibody reaction; and
 (c) instructions on how to use components (a) and (b) to carry out the diagnosis.

21. The method according to claim 4 wherein the protein is albumin and the non-antibody assay comprises use of an albumin specific dye to test for native and intact modified albumin.

22. The method according to claim 6, wherein the protein is globulin.

23. The method of claim 4 wherein the protein is selected from albumin, transferrin and IgG.

24. The method according to claim 14 wherein the protein is albumin and the non-antibody assay comprises use of an albumin specific dye to test for native and intact modified albumin.

* * * * *